United States Patent
Chen et al.

(10) Patent No.: US 8,801,966 B2
(45) Date of Patent: Aug. 12, 2014

(54) LIQUID CRYSTALS COMPRISING CYCLOPENTANE GROUPS

(75) Inventors: Xinhua Chen, Erie, CO (US); R. Amaranatha Reddy, Boulder, CO (US)

(73) Assignee: VVI Bright China Ltd., Nanjing (CN)

( * ) Notice: Subject to any disclaimer, the term of this patent is extended or adjusted under 35 U.S.C. 154(b) by 158 days.

(21) Appl. No.: 12/866,295

(22) PCT Filed: Feb. 5, 2009

(86) PCT No.: PCT/US2009/033197
§ 371 (c)(1),
(2), (4) Date: Dec. 17, 2010

(87) PCT Pub. No.: WO2009/100204
PCT Pub. Date: Aug. 13, 2009

(65) Prior Publication Data
US 2011/0089374 A1    Apr. 21, 2011

Related U.S. Application Data

(60) Provisional application No. 61/027,230, filed on Feb. 8, 2008.

(51) Int. Cl.
| | |
|---|---|
| C09K 19/30 | (2006.01) |
| C09K 19/52 | (2006.01) |
| C09K 19/06 | (2006.01) |
| C09K 19/34 | (2006.01) |
| C09K 19/32 | (2006.01) |
| C09K 19/00 | (2006.01) |
| C07C 17/00 | (2006.01) |
| C07C 19/00 | (2006.01) |
| C07C 21/00 | (2006.01) |
| C07C 23/00 | (2006.01) |
| C07C 22/00 | (2006.01) |

(52) U.S. Cl.
CPC ................ C09K 19/30 (2013.01)
USPC ............ 252/299.63; 252/299.01; 252/299.6; 252/299.61; 252/299.62; 428/1.1; 349/182; 570/101; 570/123; 570/124; 570/127; 570/129

(58) Field of Classification Search
USPC ............ 252/299.01, 299.6, 299.62, 299.63; 428/1.1; 349/182; 570/101, 123, 124, 570/127, 129
See application file for complete search history.

(56) References Cited

U.S. PATENT DOCUMENTS

| | | | |
|---|---|---|---|
| 4,873,019 A | 10/1989 | Krause et al. | |
| 5,271,864 A | 12/1993 | Wand et al. | |
| 5,759,443 A * | 6/1998 | Funfschilling et al. .. | 252/299.61 |
| 6,413,448 B1 | 7/2002 | Wand et al. | |
| 6,500,503 B2 | 12/2002 | Shibata et al. | |
| 6,693,223 B1 | 2/2004 | Takeuchi et al. | |
| 7,052,742 B1 * | 5/2006 | Hornung et al. ............... | 428/1.1 |
| 7,122,228 B2 | 10/2006 | Reiffenrath et al. | |
| 2004/0232382 A1 | 11/2004 | Okamura et al. | |
| 2006/0202163 A1 | 9/2006 | Lietzau et al. | |
| 2011/0309300 A1 | 12/2011 | Masukawa et al. | |

FOREIGN PATENT DOCUMENTS

| | | |
|---|---|---|
| CN | 1168365 A | 12/1997 |
| CN | 1928001 A | 3/2007 |
| EP | 0 789 067 A1 | 8/1997 |
| EP | 0 821 049 A1 | 1/1998 |
| EP | 0 821 049 B1 | 1/2001 |
| JP | 10072386 A | 3/1998 |

OTHER PUBLICATIONS

Khoo et al., Optics and Nonlinear Optics of Liquid Crystals, World Scientific Publishing Co. Pte. Ltd., Singapore, Dec. 31, 1993, pp. 167-170.
Khoo I.-C. et al., Optics and Nonlinear Optics of Liquid Crystals, Series in NonLinear Optics, vol. 1, pp. 168-169, Apr. 1993.

* cited by examiner

*Primary Examiner* — Geraldina Visconti
(74) *Attorney, Agent, or Firm* — Lathrop & Gage LLP

(57) ABSTRACT

Provided are liquid crystal compounds and mixtures incorporating the same. The liquid crystal compounds of the invention generally comprise a cyclopentane group and at least two other rings. In one embodiment, the liquid crystal compounds of the invention comprise a cyclopentane group and at least two other rings, one of which is a fused ring system.

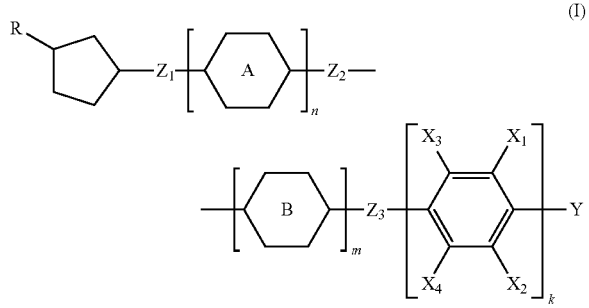

30 Claims, No Drawings

LIQUID CRYSTALS COMPRISING CYCLOPENTANE GROUPS

CROSS-REFERENCE TO RELATED APPLICATIONS

This application is the U.S. National Stage of International Application No. PCT/US2009/033197, filed Feb. 5, 2009, which claims the benefit of U.S. Provisional Application Ser. No. 61/027,230, filed Feb. 8, 2008, both of which are hereby incorporated by reference to the extent not inconsistent with the disclosure herewith.

BACKGROUND OF THE INVENTION

Liquid crystal displays use mixtures of liquid crystals having desired material properties such as operating temperature range, thermal stability, light stability, switching time, and contrast ratio. The properties of the mixtures and devices are determined by the constituents of the mixtures.

The demand for liquid crystal displays having improved performance has increased. In particular, liquid crystal mixtures having low threshold voltage are desired, especially for display applications. The threshold voltage is the amount of voltage needed to apply across a pixel to produce a response. Addressing pixels with lower voltages allows simplification of the electronics used, resulting in the possibility for space and weight savings. The threshold voltage is inversely proportional to the dielectric anisotropy of the mixture. Therefore, one way to produce a liquid crystal mixture having a low threshold voltage is the use of mixtures having a large (positive or negative) dielectric constant.

U.S. Pat. No. 5,759,443, U.S. Pat. No. 4,873,019, CN 1928001 A, and EP patent application EP0789067A1 disclose certain compounds having cyclopentyl groups.

There is a continuing need in the art for improved liquid crystal compounds and mixtures.

BRIEF SUMMARY OF THE INVENTION

Provided are liquid crystal compounds and mixtures incorporating the same. The liquid crystal compounds of the invention generally comprise a cyclopentane group and at least two other rings. In one embodiment, the liquid crystal compounds of the invention comprise a cyclopentane group and at least two other rings, one of which is a fused ring system. In one embodiment, the liquid crystal compounds of the invention comprise a terminal cyclopentane group and at least two other rings, one of which is a fused ring system. More specifically, compounds of the invention have general Formula I:

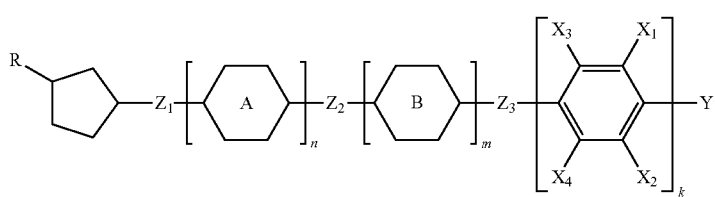

Formula I wherein

R is selected from the group consisting of H and unsubstituted or substituted alkyl each having 1-12 carbon atoms wherein the substitutions are independently one or more of halogen or —CN, wherein one or more —$CH_2$ groups of the alkyl groups may independently be replaced with —O—, —S—, —CO—, —CO—O—, —O—CO—, —O—CO—O— or —CH=CH—, provided that heteroatoms are not connected directly, except as permitted in the listed groups;

A and B are each independently selected from the group consisting of: 1,4-cyclohexylene, in which one —$CH_2$— or two not directly linked —$CH_2$— can be replaced by —O— or —S—; 1,4-cyclohexenylene; piperidine-1,4-diyl; 1,4-bicyclo[2,2,2]octylene; 1,4-phenyl; pyridin-5,2-diyl; pyrimidin-5,2-diyl; naphthalene-2,6-diyl; trans-decahydronaphthalene-2,6-diyl; tetrahydronaphthalene-2,6-diyl; indanediyl; indenediyl; phenanthrenediyl; and dibenzofurandiyl, which may each independently in each instance be substituted with one or more halogens and/or one or more $X_1$-$X_4$ substituents;

$Z_1$ is a single bond or C1-C7 unsubstituted or substituted alkylene, wherein the substitutions are independently one or more of halogen or —CN, wherein one or more —$CH_2$— groups of the alkyl groups may each independently be replaced by —O—, —S—, —CO—O—, —O—CO—, —O—CO—O— or —CH=CH— provided that heteroatoms are not connected directly to each other except as permitted in the listed groups;

$Z_2$ and $Z_3$ are each independently selected from the group consisting of: a single bond, —$(CH_2)_2$—, —$(CH_2)_4$—, —CH=CH$CH_2$$CH_2$—, —$CH_2$$CH_2$CH=CH—, —$CF_2$O—, —$OCF_2$—, —$CF_2$$CF_2$—, —CF=CF—, —$CH_2$$CF_2$—, —$CF_2$$CH_2$—, —$OCF_2$$CF_2$O—, —$C_2H_4$$CF_2$O—, —$CH_2$$CF_2$$OCH_2$—, —$CH_2$$OCF_2$$CH_2$—, —$OCF_2$$C_2H_4$—, —$C_3H_6$O—, —$OC_3H_6$—, —$C_2H_4$$OCH_2$—, —$CH_2$$OC_2H_4$—, —$CH_2$O—, —$OCH_2$—, —CH=CH—, —C≡C—, and —COO—;

n, m and K are each independently 0, 1, or 2, and m+K+n≥2;

$X_1$, $X_2$, $X_3$, and $X_4$ are each independently selected from the group consisting of: —H, —F, —Cl, —$CF_3$, —$CHF_2$, —$OCF_3$—$OCF_2$H and —CN;

Y is independently selected from the group consisting of: —H, —F, —Cl, —CN, —NCS, —$OCHF_2$, —$CHF_2$, —$OCF_3$, —$OCF_2$$CF_3$, —$CF_3$, $C_{1-20}$ alkyl, $C_{1-20}$ alkoxy, $C_{1-20}$ alkenyl, and $C_{1-20}$ alkenyloxy, wherein the alkyl, alkoxy, alkenyl, and alkenyloxy groups may be independently substituted by one or more halogens;

wherein one or more hydrogen atoms in Formula I may be replaced with deuterium;

provided that when R=H and Y has less than 2 carbon atoms and $X_3$, $X_4$ are H or when R=H and Y has two or more carbon atoms and $Z_1$ has more than 3 carbon atoms, there must be a fused ring system present in the compound or one of $Z_1$, $Z_2$ and $Z_3$ must be selected from the group consisting of: C1-C3 alkylene, —CH=CH$CH_2$$CH_2$—, —$CH_2$$CH_2$CH=CH—, —$CF_2$O—, —$OCF_2$—, —$CF_2$$CF_2$—, —CF=CF—, —$CH_2$$CF_2$—, —$CF_2$$CH_2$—, —$OCF_2$$CF_2$O—, —$C_2H_4$$CF_2$O—, —CH2CF2OCH2—, —CH2OCF2CH2—, —$OCF_2$$C_2H_4$—, —$C_3H_6$O—, —$OC_3H_6$—, —$C_2H_4$$OCH_2$—, —$CH_2$$OC_2H_4$—, and —CH=CH—;

and provided that when R is not H and Y does not contain a —CF$_2$— group, either one of A and B is selected from the group consisting of: 1,4-cyclohexylene, in which one or two not directly linked —CH$_2$— groups can be replaced by —O— or —S—; pyridin-5,2-diyl; pyrimidin-5,2-diyl; indanediyl; indenediyl; phenanthrenediyl; and dibenzofurandiyl; or one of Z$_1$, Z$_2$ and Z$_3$ must be selected from the group consisting of: —(CH$_2$)$_4$—, —CH═CHCH$_2$CH$_2$—, —CH$_2$CH$_2$CH═CH—, —CF$_2$O—, —OCF$_2$—, —CF$_2$CF$_2$—, —CF═CF—, —CH$_2$CF$_2$—, —CF$_2$CH$_2$—, —OCF$_2$CF$_2$O—, —C2H$_4$CF$_2$O—, —CH$_2$CF$_2$OCH$_2$—, —CH$_2$OCF$_2$CH$_2$—, —OCF$_2$C$_2$H$_4$—, —C$_3$H$_6$O—, —OC$_3$H$_6$—, —C$_2$H$_4$OCH$_2$—, —CH$_2$OC$_2$H$_4$—, —CH═CH—, and —C≡C—.

In an embodiment, X$_1$, X$_2$, X$_3$, and X$_4$ are each independently selected from the group consisting of: —H, —F, —Cl, —CF$_3$, —CHF$_2$ and —CN.

If not specified, any group, for example a ring structure, may be attached in any suitable location. If there are two or more rings linked together, for example, when n, m or k is not 0, it is noted that each of the rings may be the same of different. As an example of this, when n is 2, the two "A" rings do not need to be the same, although they may be in certain embodiments. When used herein, "indane" means:

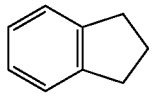

which is attached to the remainder of the structure in any suitable location(s). When used herein, "indene" means:

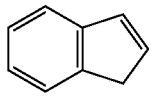

which is attached to the remainder of the structure in any suitable location(s). When linked as an A or B ring, the indane and indene groups are called indanediyl and indenediyl groups.

As used herein, a "single bond" as a variable means that there is a direct linkage between two structures. For example, if Z$_1$ is a single bond and n is 1, there is a direct linkage between the cyclopentane ring and the A ring. As used herein, a "fused ring system" has at least two rings joined together at at least two atoms. 1,4-bicyclo[2.2.2]octylene; naphthalene-2,6-diyl; decahydronaphthalene-2,6-diyl; tetrahydronaphthalene-2,6-diyl; indanediyl; indenediyl; phenanthrenediyl; and dibenzofurandiyl are all examples of fused ring systems. As used herein, halogen means fluorine, chlorine, bromine or iodine.

In one embodiment, there is at least one fused ring in a compound of the invention. In one embodiment, a compound of the invention is one of I-11 through I-17. In one embodiment, a compound of the invention is one of I-23 through I-27. In one embodiment, a compound of the invention is one of I-33 through I-35. In an embodiment, a compound of the invention is one of I-36 through I-47. In one embodiment, a compound of the invention has R═H and a fused ring system.

In an embodiment, one or more hydrogen atoms on one or more rings is replaced with deuterium. In an embodiment, one or more hydrogen atoms on a non-ring structure is replaced with deuterium.

In separate embodiments, the cyclopentene ring has one of the structures below:

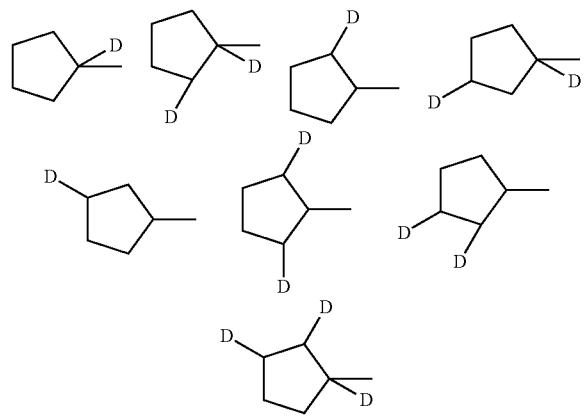

All possible locations of one or more deuterium substitution for hydrogen in the structures shown and described herein are intended to be included to the same extent as if they were individually shown.

DETAILED DESCRIPTION OF THE INVENTION

The following non-limiting description provides examples of some embodiments of the invention.

The use of one or more compounds of the invention in mixtures having desired properties for various liquid crystal applications is known to one of ordinary skill in the art without undue experimentation.

Devices comprising one or more compounds of the invention can be made and operated by one of ordinary skill in the art without undue experimentation.

The description herein provides some additional exemplary embodiments of the invention and variables which can be separate or combined together in all possible permutations, independently and in combination, to formulate compounds of the invention.

The compounds of the invention have a high dielectric constant which may be positive or negative. The use of compounds and mixtures having negative or positive dielectric constants is known in the art. In some embodiments of the invention, the compounds have positive dielectric constant of at least 8. In some embodiments of the invention, the compounds have a negative dielectric constant of −2 or less. Larger positive and larger negative numbers are desired.

Positive Dielectric Constant Compounds

Specific particular embodiments of compounds of the invention having positive dielectric constants are shown below in structures I-1 through I-17, where the variables have the following definitions:

Y is independently selected from the group consisting of: —F, —Cl, —CF$_3$, —OCF$_3$, —OCHF$_2$, —OCF$_2$CF$_3$, —OCF═CF$_2$, —OCHFCF$_3$, —OCF$_2$CF═CF$_2$;

X$_1$, X$_2$, X$_3$, X$_4$ are each, independently of one another, —H or —F;

Z is independently selected from the group consisting of: single bond, —C$_2$H$_4$—CF$_2$O—, —CF═CF—, —C$_2$F$_4$—; —CO$_2$—, —C$_4$H$_8$—, —C$_2$H$_4$CF$_2$O—, —OCF$_2$CF$_2$O—, —CH═CHCH$_2$CH$_2$—, —CH$_2$CH$_2$CH═CH—; and R is C1-C12 alkyl or H.

I-1
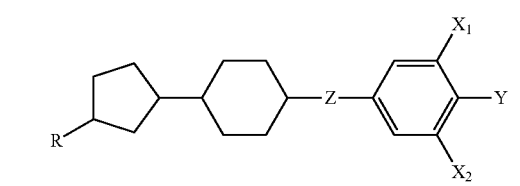
I-2
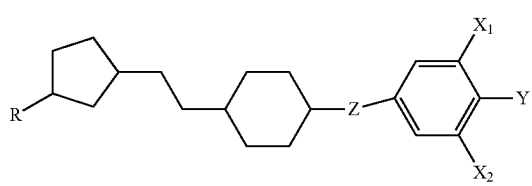
I-3
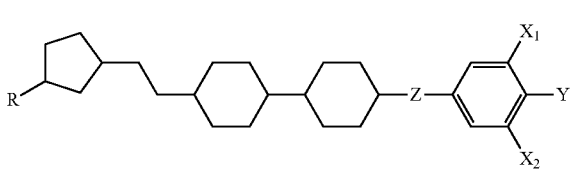
I-4
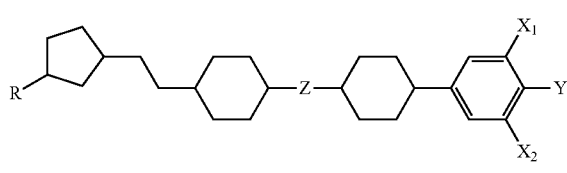
I-5
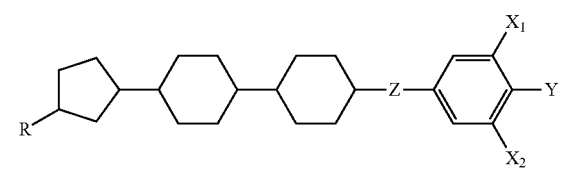
I-6
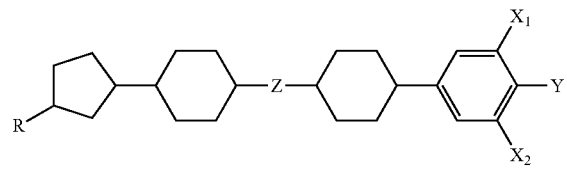
I-7
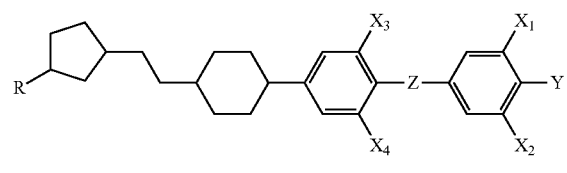
I-8
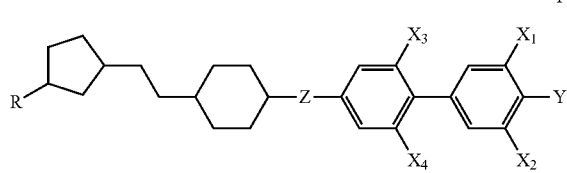
-continued
I-9
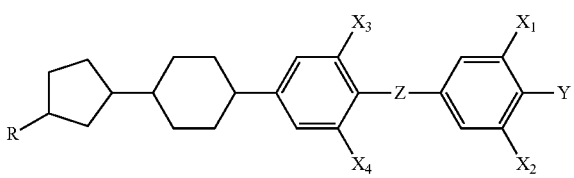
I-10
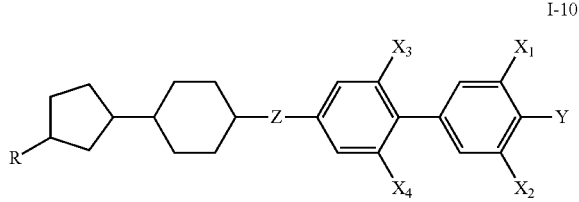
I-11
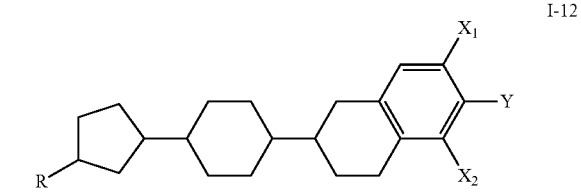
I-12
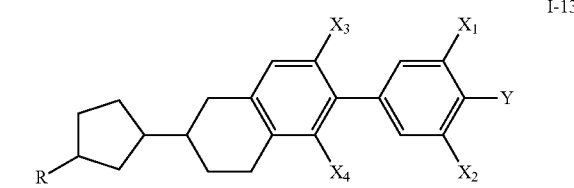
I-13
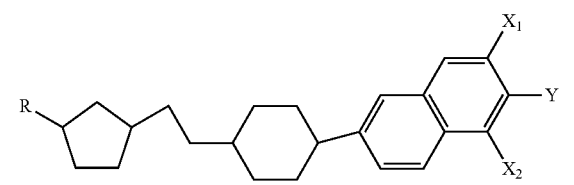
I-14
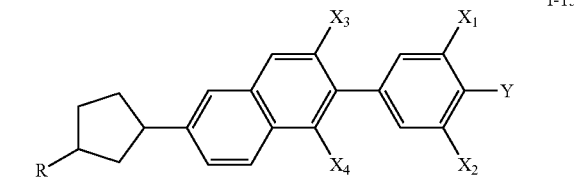
I-15
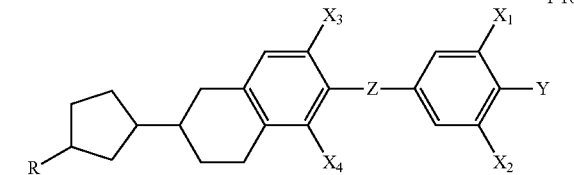
I-16

I-17

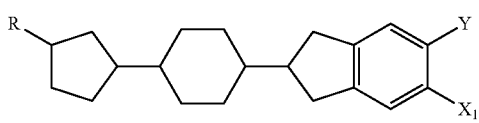

Negative Dielectric Constant Compounds

Specific particular embodiments of compounds of the invention having positive dielectric constants are shown below in structures I-18 through I-47, where the variables have the following definitions:

R is —H or C1-C7 n-alkyl;

R' is C1-C7 n-alkyl or C1-C7 alkoxy;

$X_1$ and $X_2$ are each independently selected from the group consisting of —F, —Cl, —CF$_3$, —CHF$_2$, —OCF$_3$ and —OCF$_2$H;

$X_3$, $X_4$, $X_5$ and $X_6$ are each independently —H or —F;

Z is independently single bond, —C$_2$H$_4$—, —C$_4$H$_8$—, —CF$_2$O—, —CF=CF—, —C$_2$F$_4$—, —C$_2$H$_4$CF$_2$O— or —CO$_2$—.

I-18

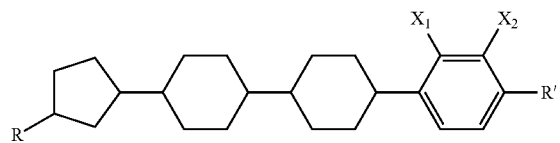

I-19

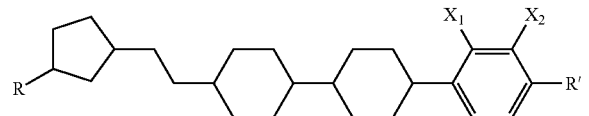

I-20

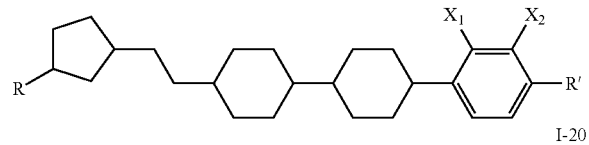

I-21

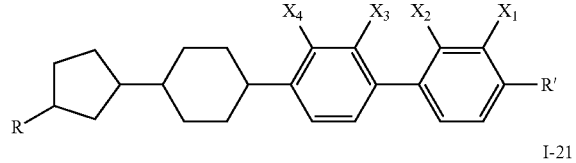

I-22

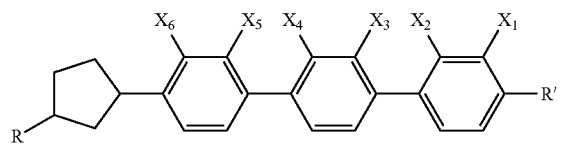

I-23

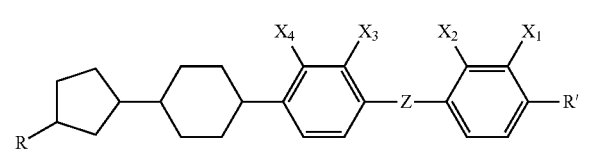

I-24

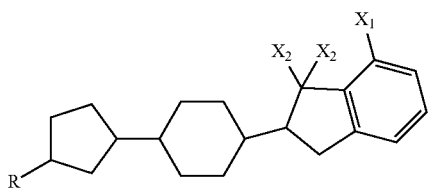

I-25

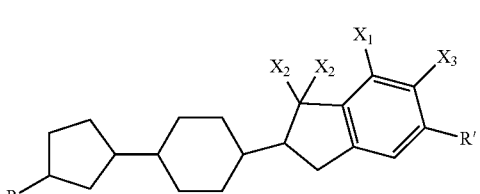

I-26

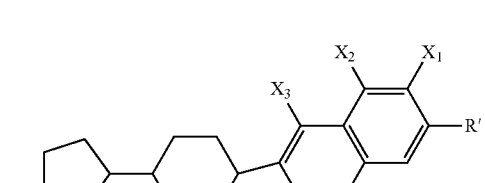

I-27

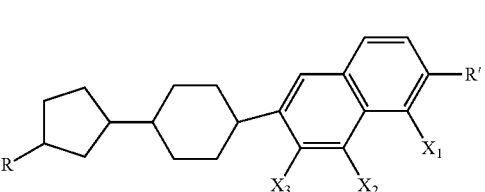

I-28

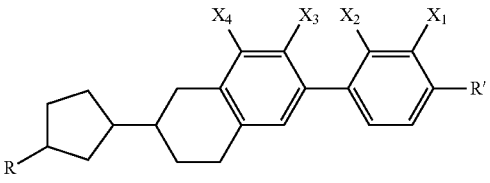

I-29

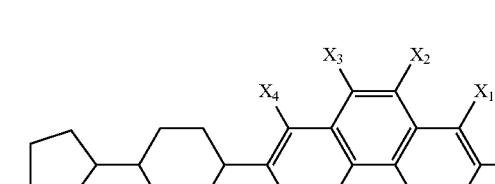

I-30

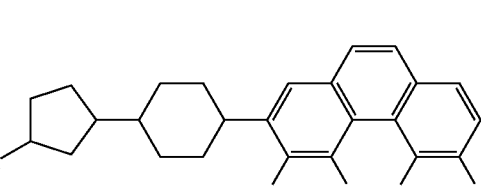

I-31

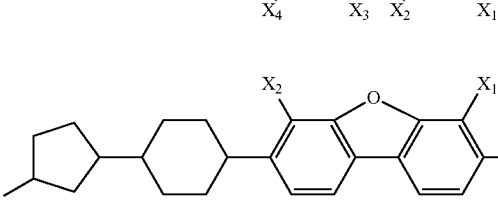

I-32
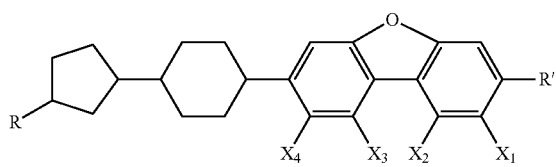

I-33
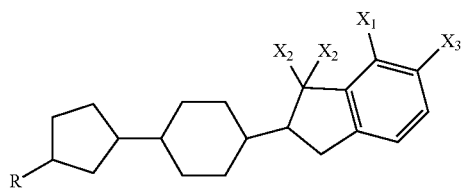

I-34
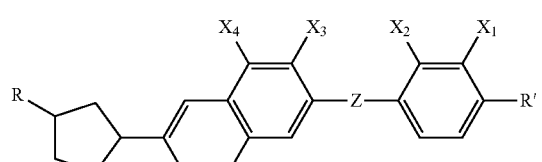

I-35
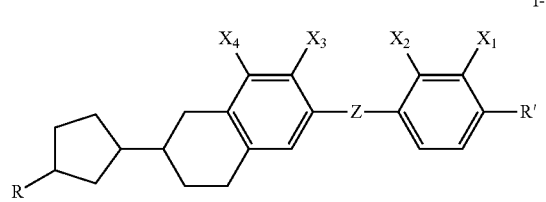

I-36
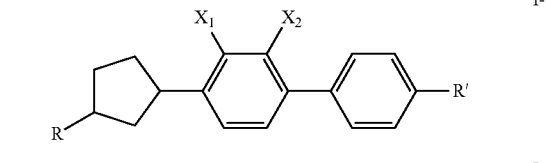

I-37
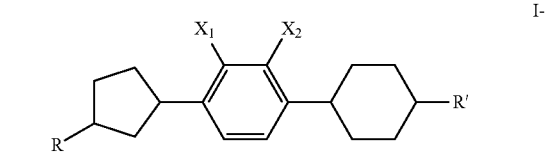

I-38
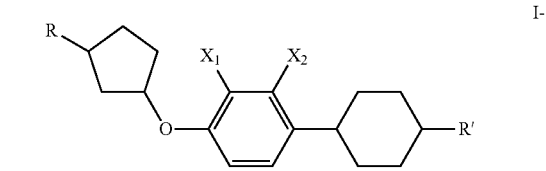

I-39
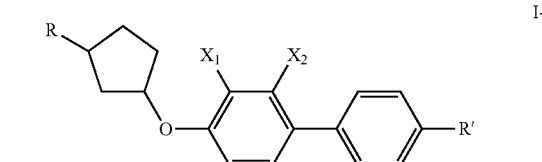

I-40
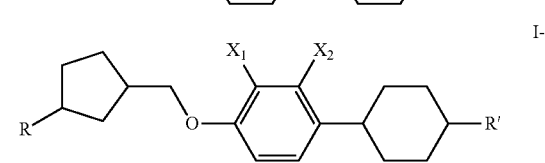

I-41
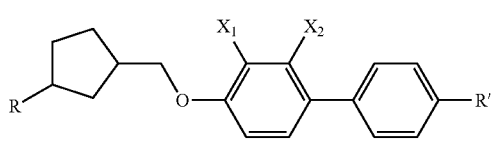

I-42
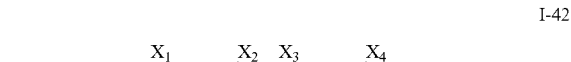

I-43
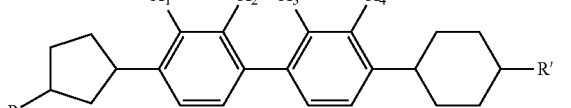

I-44
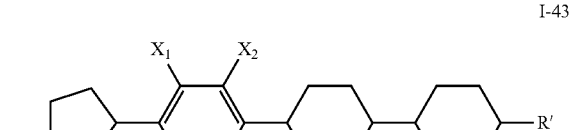

I-45
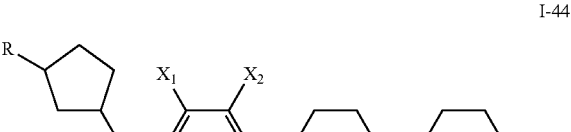

I-46
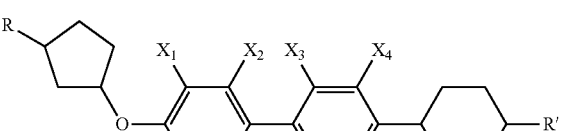

I-47
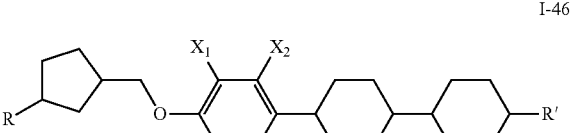

Mixtures

As known in the art, there are typically many components of liquid crystal mixtures, as determined by the desired use of the mixture. The composition of the liquid crystal mixtures of the invention can be determined by one having ordinary skill in the art without undue experimentation. The addition of one or more compounds of the invention in liquid crystal mixtures improves the properties of the mixture, including lowering threshold voltage, increasing switching speed and other properties which are known in the art.

Positive Dielectric Constant Mixture

The compounds of the invention may be used as components in any desired liquid crystal mixture, such as those mixtures known in the art. In one embodiment, the liquid crystal mixture comprises one or more compounds of Formula I. In one embodiment, the liquid crystal mixture has positive dielectric constant. In one embodiment, the liquid crystal mixture having positive dielectric constant comprises one or more compounds of Formula I-1 through I-17.

The mixture may include one or more compounds of Formula I and one or more compounds of Formula II-XVI:

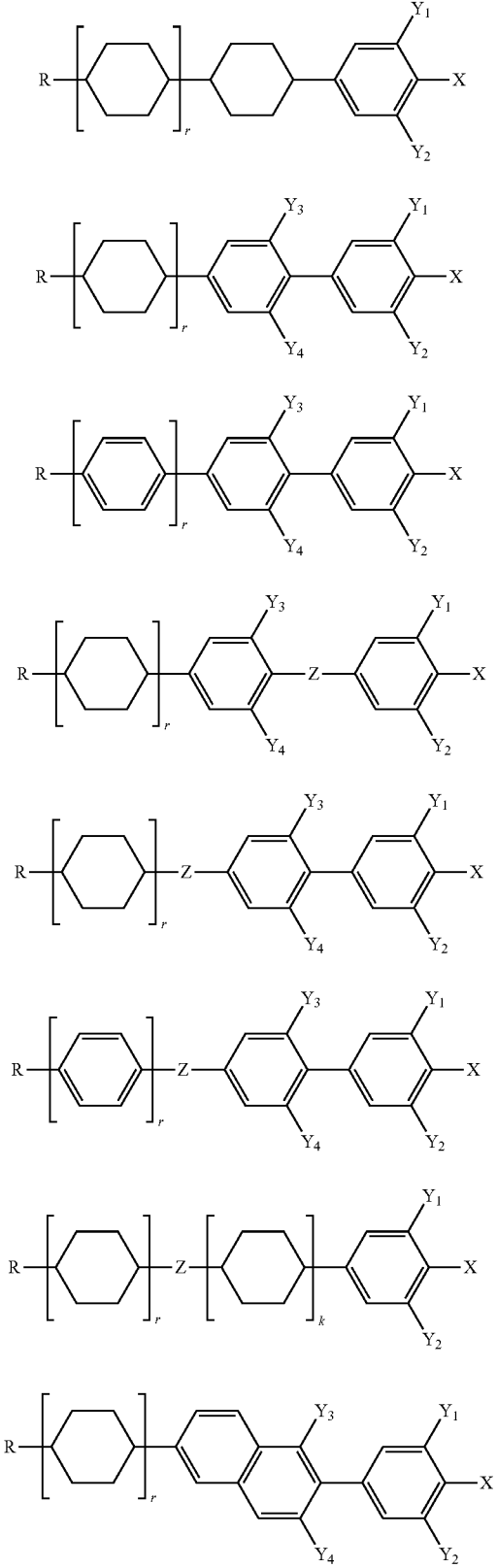
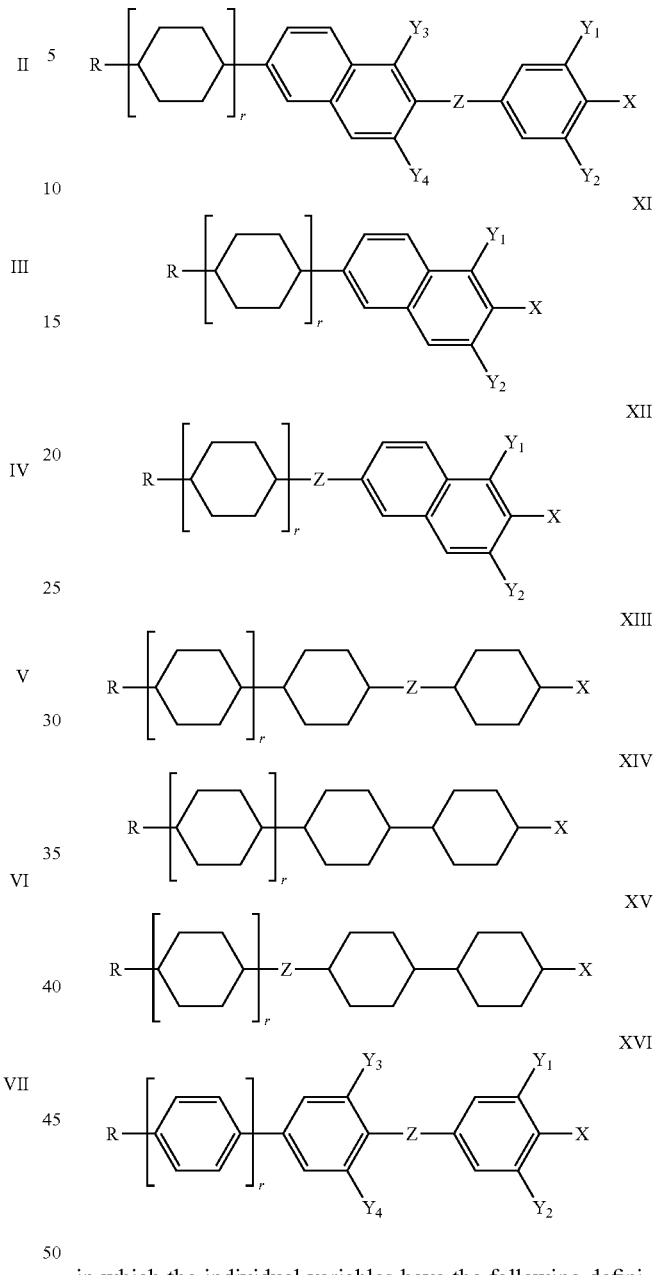

in which the individual variables have the following definitions:

R is C1-C9 n-alkyl, C1-C9 alkoxy, C1-C9 oxaalkyl, C1-C9 fluoroalkyl or C1-C9 alkenyl;

X is —F, —Cl, halogenated C1-C6 alkyl, halogenated C1-C6 alkenyl, halogenated C1-C6 alkenyloxy or halogenated C1-C6 alkoxy;

Z is —$C_2H_4$—, —$C_4H_8$—, —CH=CH—, —$CH_2O$—, —COO—, —$OCH_2$—, —$OCF_2$—, —$CF_2O$—, —CF=CF—, —$C_2F_4$—, —$CH_2CF_2$— or —$CF_2CH_2$—;

$Y_1$, $Y_2$, $Y_3$ and $Y_4$ are each, independently of one another, —H or —F; and r is 0, 1 or 2; and k is 0 or 1, provided that if both r and k appear in the same formula, r+k≥2.

Additional specific examples of compounds which may be included in a mixture are shown below where R is as defined for compounds II-XVI:

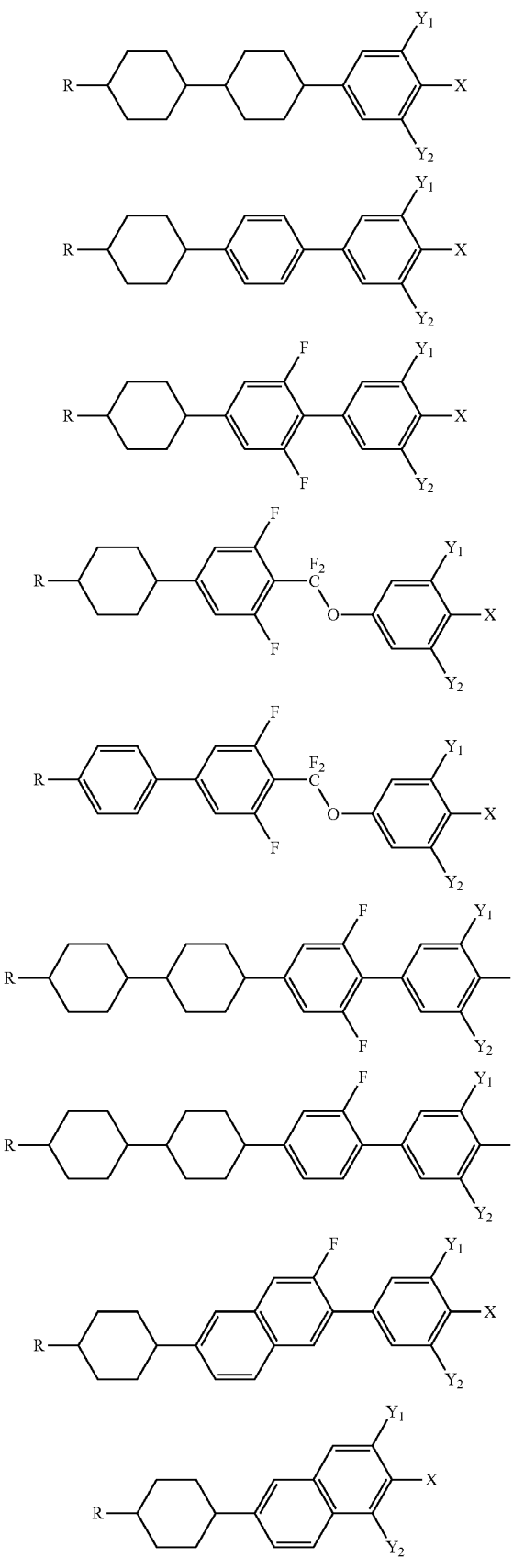
In each of the formulas shown herein, the structure:
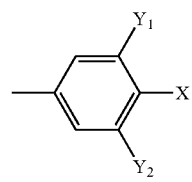
may have any of the following formulas:
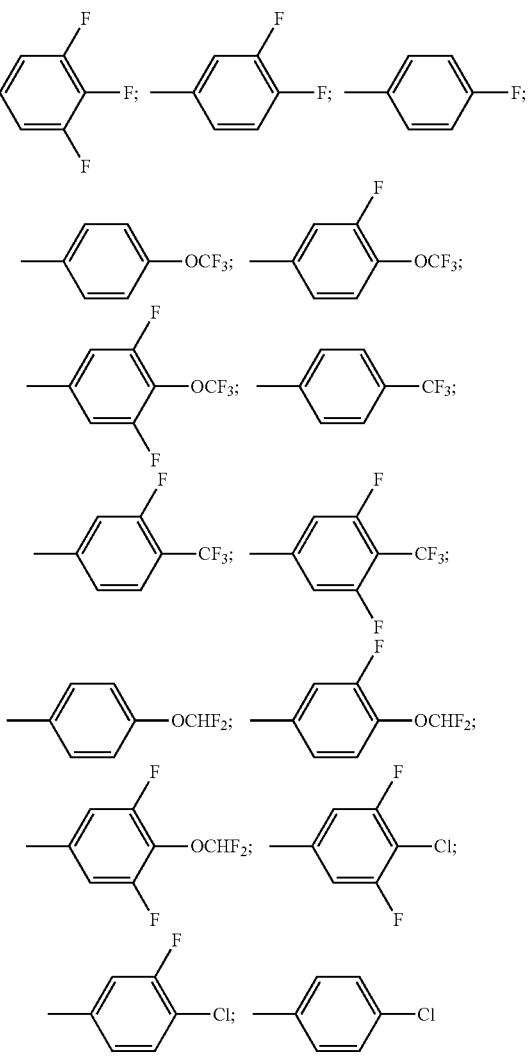
In other embodiments, the mixture may comprise one or more compounds of Formula I and one or more compounds selected from the group consisting of compounds of the structure below XVII-XXIII.
XVII
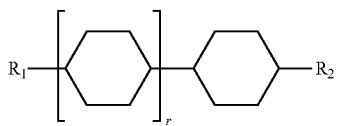

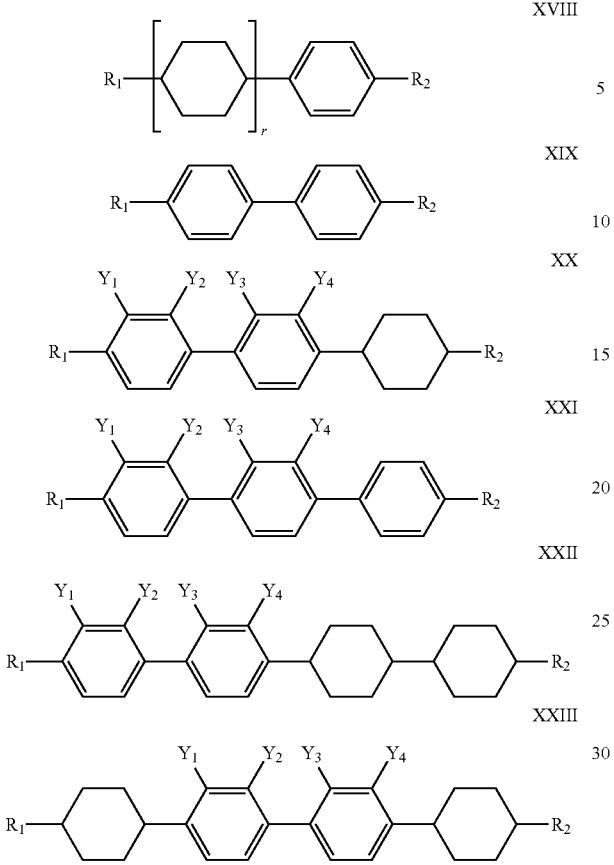
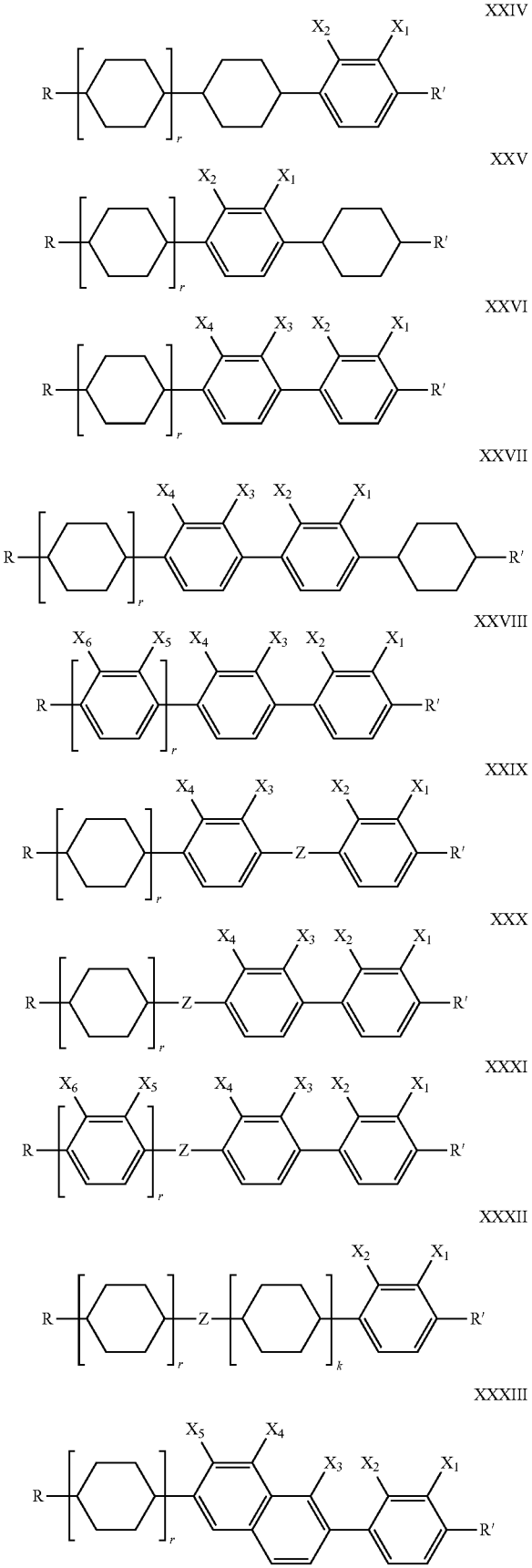

where the variables have the following definitions:
$R_1$ and $R_2$ are each independently C1-C9 n-alkyl, C1-C9 alkoxy, C1-C9 oxaalkyl, or C1-C9 alkenyl;
$Y_1, Y_2, Y_3$ and $Y_4$ are each, independently of one another, —H or —F, and
r is 0, 1 or 2.

Negative Dielectric Constant Mixtures

In one embodiment, the liquid crystal mixture has negative dielectric constant. In one embodiment, the liquid crystal mixture having negative dielectric constant comprises one or more compound of Formula I-18 through I-47. In another embodiment, the liquid crystal mixture having negative dielectric constant comprises one or more compounds of Formula I, such as I-18 to I-47 and additionally comprises a useful amount of one or more compounds selected from the group consisting of compounds of the general formulae XXIV to XLIV, where the variables are as defined below:
R is C1-C8 n-alkyl, C1-C8 alkoxy, C1-C8 alkenyl or C1-C8 alkenyloxy;
R' is C1-C8 alkyl, C1-C8 alkoxy, C1-C8 alkenyl or C1-C8 alkenyloxy;
$X_1, X_2, X_3, X_4, X_5$ and $X_6$ are independently selected from the group consisting of: —H, —F, —Cl, —CHF$_2$, —CF$_3$, —OCF$_3$ and —OCHF$_2$; with the proviso that at least two from $X_1$ to $X_6$ are —F, —Cl, —CHF$_2$ or —CF$_3$;
Z is independently selected from the group consisting of: single bond, —C$_2$H$_4$—, —C$_4$H$_8$—, —CH=CHCH$_2$CH$_2$—, —CH$_2$CH$_2$CH=CH—, —CF$_2$O—, —OCF$_2$—, —CF=CF—, —C$_2$F$_4$—, —C$_2$H$_4$CF$_2$O—, —OCF$_2$C$_2$H$_4$— and —CO$_2$—;
r is 0, 1 or 2; k is 0 or 1, providing that r+k≥2.

XXXIV
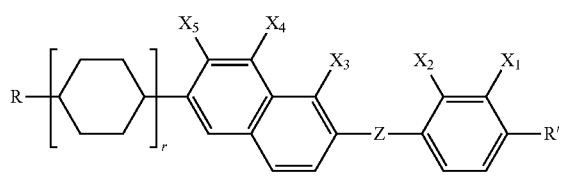

XXXV
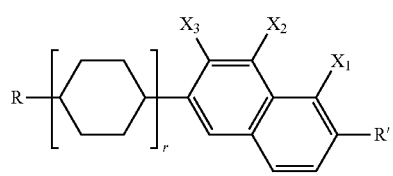

XXXVI
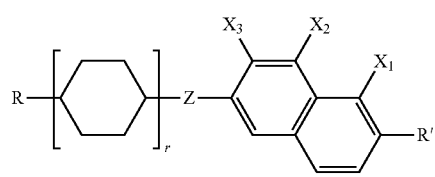

XXXVII
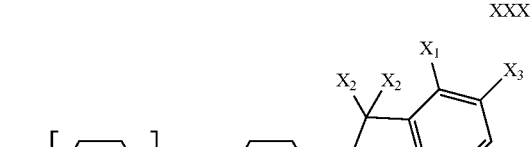

XXXVIII
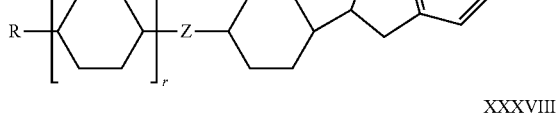

XXXIX
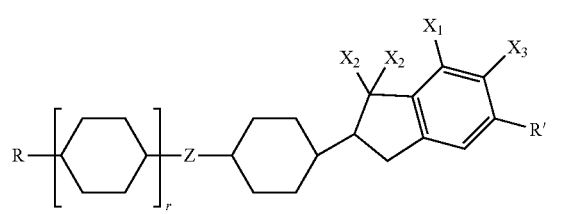

XL
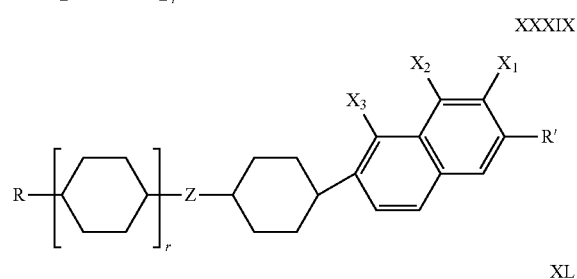

XLI
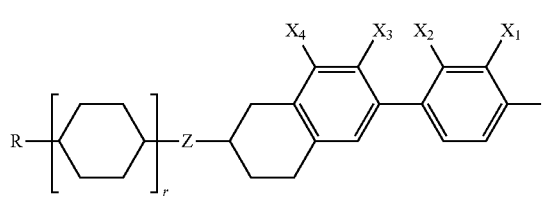

XLII
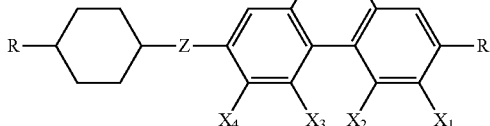

XLIII
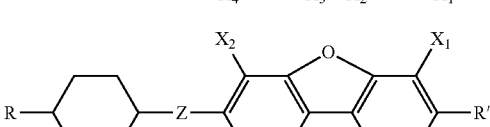

XLIV
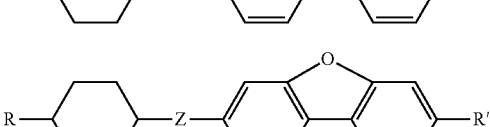

In other specific embodiments, the negative dielectric constant mixture may comprise one or more compounds of Formula I and one or more compounds selected from the group consisting of compounds of formulas XLV-XLVIII below.

XLV
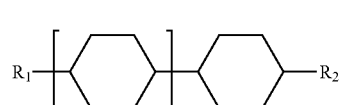

XLVI
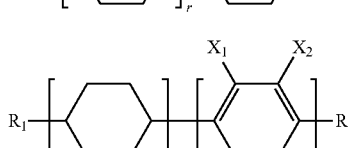

XLVII
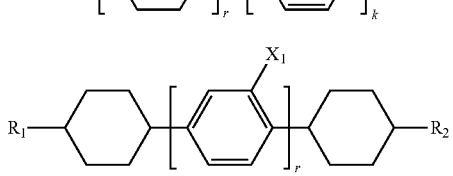

XLVIII
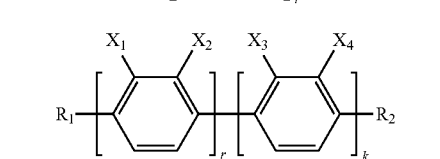

in which the individual variables have the following definitions:

$R_1$ and $R_2$ are each independently C1-C8 n-alkyl, C1-C8 alkoxy, C1-C8 oxaalkyl, C1-C8 alkenyl, or C1-C8 alkenyloxy;

$X_1$, $X_2$, $X_3$, and $X_4$ are —H or —F, provided that only one of $X_1$, $X_2$, $X_3$, and $X_4$ may be F in the same compound;

r is 1 or 2; k is 1 or 2.

The compounds of the invention may be used in any useful amount in a liquid crystal mixture, including less than 0.1% by weight of the total composition; less than 0.5% by weight of the total composition; less than 1% by weight of the total composition, less than 3% by weight of the total composition; less than 5% by weight of the total composition; less than 7% by weight of the total composition; less than 10% by weight of the total composition; less than 20% by weight of the total composition; less than 25% by weight of the total composition; less than 30% by weight of the total composition; less than 35% by weight of the total composition; less than 40% by weight of the total composition; less than 50% by weight of the total composition; and any other useful amount.

In one embodiment, there is between 0.5% and 80% of one or more compounds of Formula I. In one embodiment, there is between 0.5% and 80% of one or more compounds of Formula I-1 through I-17. In one embodiment, there is between 0.5% and 80% of one or more compounds of Formula I-18 through I-35. In one embodiment, there is between 0.5% and 80% of one or more compounds of Formula I, and between 0.5% and 80% or one or more compounds of a compound of formula II-XVI In one embodiment, there is between 0.5% and 80% of one or more compounds of Formula I, and between 0.5% and 80% of one or more compounds of Formula XVII-XXIII. In one embodiment, there is between 0.5% and 80% of one or more compounds of Formula I, between 0.5% and 80% or one or more compounds of Formula II-XVI, and between 0.5% and 80% of one or more compounds of Formula XVII-XXIII. In one embodiment, there is between 0.5% and 80% of one or more compounds of Formula I, and between 0.5% and 80% or one or more compounds of a compound of formula XXIV-XLIV. In one embodiment, there is between 0.5% and 80% of one or more compounds of Formula I, and between 0.5% and 80% of one or more compounds of Formula XLV-XLVIII. In one embodiment, there is between 0.5% and 80% of one or more compounds of Formula I, between 0.5% and 80% or one or more compounds of Formula XXIV-XLIV, and between 0.5% and 80% of one or more compounds of Formula XLV-XLVIII. There may be other components, as known in the art.

Synthesis

The following describes exemplary synthesis reactions for compounds of the invention. Conditions for such as reaction are well-known to one of ordinary skill in the art. The synthesis of compounds of the invention not specifically exemplified here can be carried out by one of ordinary skill in the art without undue experimentation using methods known in the art.

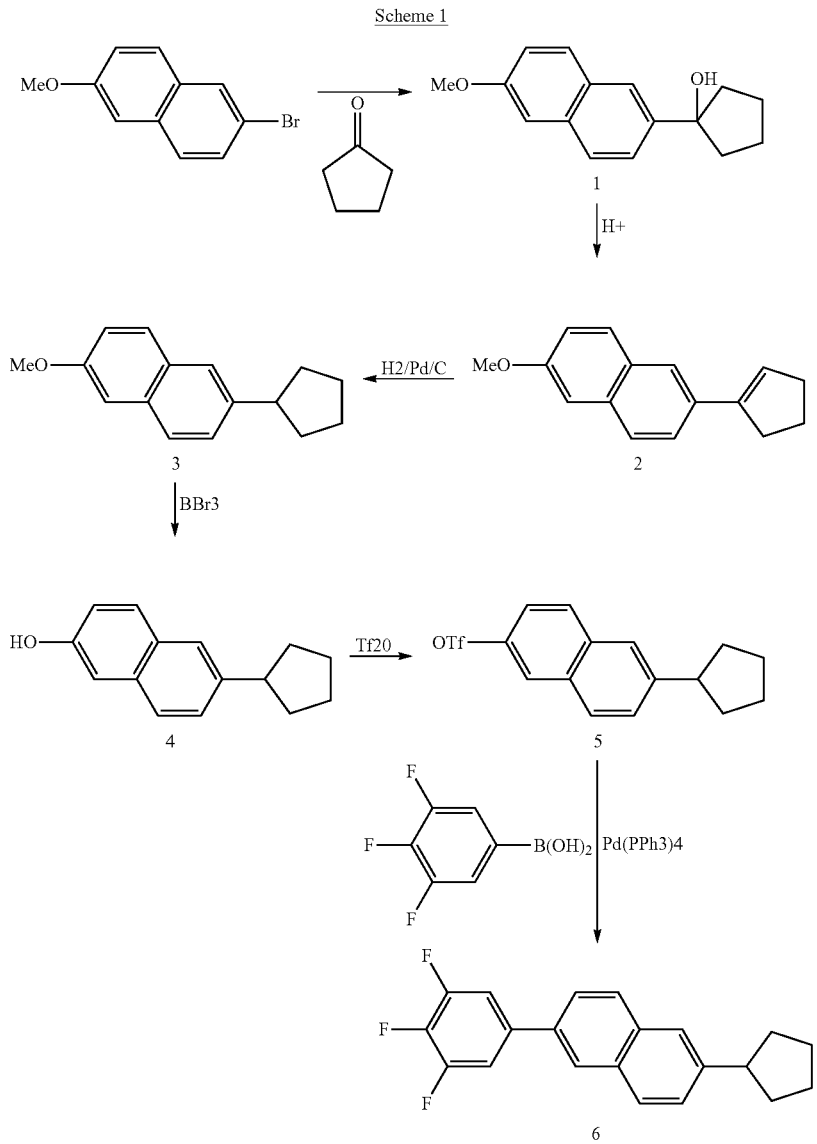

Scheme 1

EXPERIMENTAL

Synthesis of 2-Cyclopentyl-6-(3,4,5-trifluorophenyl)naphthalene

Synthesis of 1-(6-methoxynaphthalene-2-yl)cyclopentanol (Compound 1)

Grignard reagent was prepared from 6-methoxy-2-bromonaphthalene, dry Mg, a crystal of iodine and a drop of 1,2-dibromoethane in dry THF. This mixture was then cooled in an ice-sodium chloride bath, a solution of dried cyclopentanone dry THF was added drop wise via syringe. The resultant reaction mixture was then slowly warmed to room temperature. Then refluxed for additional 10 hours and cooled to room temperature, added to ice cold HCl and extracted using ethyl acetate. The combined organic extracts were washed with sat. $NH_4Cl$ solution and dried over $MgSO_4$. The crude product obtained was passed through a column of silicagel using 15% EA in hexane as eluent. Yield of the product: 70%.

2-Cyclopentenyl-6-methoxynaphthalene (Compound 2)

A solution of compound 1 in dry benzene, and a catalytic amount (2 wt %) of p-toluene-sulfonic acid were placed in a round-bottomed flask. The resulting solution was then heated at 50° C. for 15 minutes, the reaction was complete, and the resulting solution was cooled to room temperature, passed through a short pad of silicagel. Yield was almost quantitative, the product obtained was pure enough which was directly used for the next reaction.

2-Cyclopentyl-6-methoxynaphthalene (Compound 3)

To a solution of compound 2 in ethyl acetate was added a catalytic amount (5 wt %) of 5% Pd—C, the resulting solution was continued stirring vigorously until the reaction is complete. Yield was almost quantitative. The product obtained was pure enough, which was directly used for the next reaction.

6-Cyclopentylnaphthalen-2-ol (Compound 4)

A solution of compound 3 in dry dichloromethane was cooled to −78° C. in dry ice and acetone under argon. To this with stirring, a solution of BBr3 in dichloromethane was added dropwise and the resulting solution was continued stirring for additional 2 hours at this temperature and allowed to warm to room temperature overnight. The resultant solution was extracted using ethyl acetate, the crude product was crystallized from a mixture of methanol and hexane. Yield: 92%.

6-Cyclopentylnaphthalen-2-yl trifluoromethylsulfonate (Compound 5)

A solution of compound 4 and pyridine in dry dichloromethane was cooled to 5° C. using ice bath. To this with stirring, a solution of triflic anhydride in dichloromethane was added dropwise which was allowed to warm to room temperature, and continued stirring for additional 2 hours. The resultant solution was extracted using ethyl acetate, the product obtained was a low melting solid, which was directly used for the next step. Yield: 95%.

2-Cyclopentyl-6-(3,4,5-trifluorophenyl)naphthalene (compound 6)

Into a flame dried 100 ml round-bottomed flask with a magnetic stir bar, was charged with compound 5 (1.0 g, 2.9 mMol), 3,4,5-trifluorophenyl boronic acid (0.56 g, 3.19 mMol), 20 mL toluene, 2M $K_2CO_3$ (20 mL), $Bu_4NBr$ (25 mg) and the mixture flushed with argon for 10 min. [$Pd(PPh_3)_4$] (0.1 g) was added and the mixture heated under argon at ~85° C. for 12 h, with vigorous stirring. After cooling to room temperature, 25 mL water was added, extracted with 3×10 mL ethyl acetate, the organic extracts dried over $MgSO_4$, and the crude product was then passed through a column of silica gel using hexane as eluent, also crystallized from hexane. Yield, 0.89 g (94%).

Scheme 2

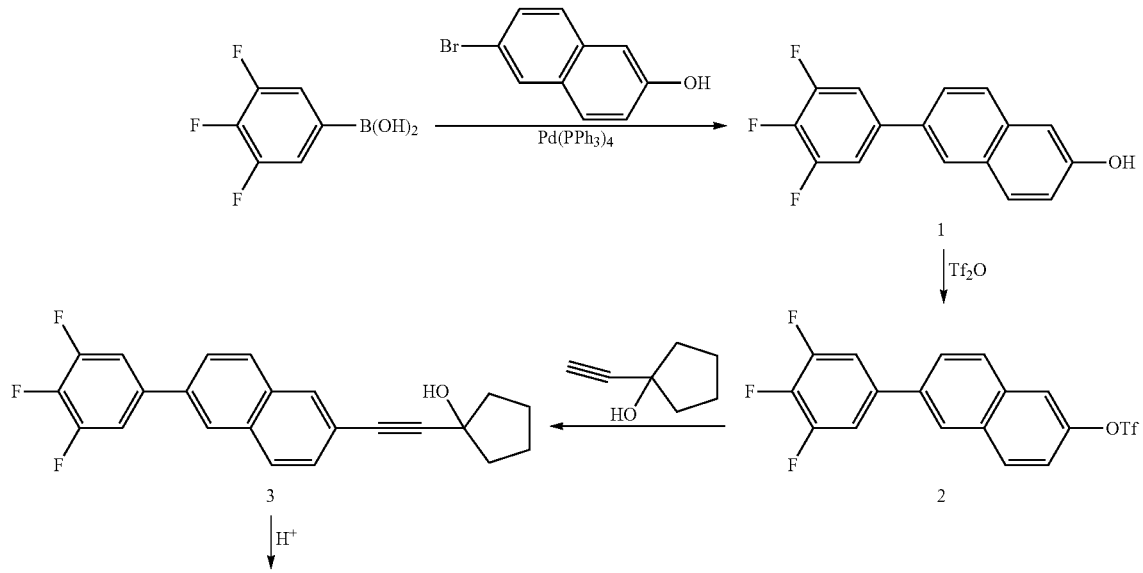

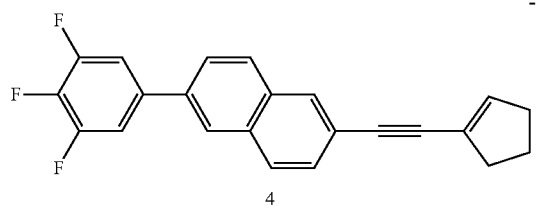

4

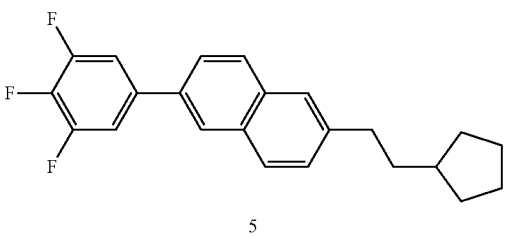

5

Synthesis of 2-(Cyclopentylethyl)-6-(3,4,5-trifluorophenyl)naphthalene 1. 6-(3,4,5-trifluorophenyl)naphthalene-2-ol (Compound 1)

A flame dried 500 ml round-bottomed flask with a magnetic stir bar, was charged with 6-hydroxy-2-bromonaphthalene (8.0 g, 35.89 mMol), 3,4,5-trifluorophenyl boronic acid (6.9 g, 39.5 mMol), 75 mL toluene, 2M $K_2CO_3$ (80 mL), $Bu_4NBr$ (50 mg) and the mixture flushed with argon for 10 min. [$Pd(PPh_3)_4$] (0.5 g) was added and the mixture heated under argon at ~85° C. overnight, with vigorous stirring. After cooling to room temperature, 50 mL water was added, extracted with 3×25 mL ethyl acetate, the organic extracts dried over $MgSO_4$, and the crude product was then crystallized from a mixture of hexane and few drops of methanol. Yield: 8 g (87%).

6-(3,4,5-trifluorophenyl)naphthalene-2-yl trifluoromethylsulfonate (Compound 2)

A solution of compound 1 and pyridine in dry dichloromethane was cooled to 5 C using ice bath. To this with stirring, a solution of triflic anhydride in dichloromethane was added drop wise which is allowed to warm to room temperature, and continued stirring for additional 2 hours. The resultant solution was extracted using ethyl acetate, the product obtained was crystallized from dichloromethane and hexane mixture. Yield: 90%.

1-((6-(3,4,5-trifluorophenyl)naphthalen-2-yl)ethynyl)cyclopentanol (Compound 3)

To a solution of triflet (compound 2) and 1-ethynylcyclopentanol in dry DMF under argon, $Pd(PPh_3)_4$, CuI and triethylamine were successively added, and the reaction mixture was stirred overnight at room temperature. The mixture was then diluted with EtOAc, washed with water and dried over MgSO4. Yield: 93%.

2-(Cyclopentylethynyl)-6-(3,4,5-trifluorophenyl) naphthalene (Compound 4)

A solution of compound 3 in dry benzene, and a catalytic amount (2 wt %) of p-toluene-sulfonic acid were placed in a round-bottomed flask. The resulting solution is then heated at 50 C for 3-4 hours, the reaction was complete, and the resulting solution was cooled to room temperature, and passed through a short pad of silicagel. The product obtained was crystallized from a mixture of hexane and dichloromethane. Yield: 90%.

5. 2-(Cyclopentylethyl)-6-(3,4,5-trifluorophenyl) naphthalene (Compound 5)

To a solution of compound 4 in ethyl acetate was added a catalytic amount (5 wt %) of 5% Pd—C, the resulting solution was continued stirring vigorously until the reaction was complete. The product obtained was crystallized from hexane. Yield 92%.

Incorporation of Deuterium into Structures:

Methods of incorporating one or more deuterium atoms into a structure are known in the art.

Characterization methods and property analysis of compounds and mixtures are well-known in the art. Methods to alter the material properties of a mixture, such as adding other compound to a mixture, or by adding more or less of a compound in a mixture, are also known in the art.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim and are intended to be able to be removed individually or collectively.

When a group of substituents is disclosed herein, it is understood that all individual members of those groups and all subgroups, including any isomers and enantiomers of the group members, and classes of compounds that can be formed using the substituents are disclosed separately. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, synthetic methods, and mixture constituents other than those specifically exemplified can be employed in the practice of the invention without resort to undue experimentation. All art-known functional equivalents, of any such methods, device elements, starting materials, synthetic methods, and mixture constituents are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The definitions are provided to clarify their specific use in the context of the invention.

One skilled in the art would readily appreciate that the present invention is well adapted to carry out the objects and obtain the ends and advantages mentioned, as well as those inherent therein. The liquid crystal compounds and methods described herein as presently representative of preferred embodiments are exemplary and are not intended as limitations on the scope of the invention. Changes therein and other uses will occur to those skilled in the art, which are encompassed within the spirit of the invention, are defined by the scope of the claims.

Although the description herein contains many specificities, these should not be construed as limiting the scope of the invention, but as merely providing illustrations of some of the embodiments of the invention. Thus, additional embodiments are within the scope of the invention and within the claims.

All references cited herein are hereby incorporated by reference to the extent that there is no inconsistency with the disclosure of this specification. Some references provided herein are incorporated by reference herein to provide details concerning additional starting materials, additional methods of synthesis, additional methods of analysis and additional uses of the invention.

We claim:

1. A compound having the formula:

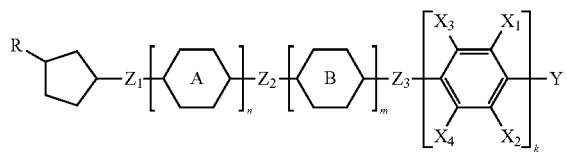

wherein

R is selected from the group consisting of hydrogen and unsubstituted or substituted alkyl each having 1-12 carbon atoms wherein the substitutions are independently one or more of halogen or CN, wherein one or more —$CH_2$— groups of the alkyl group independently are optionally replaced with —O—, —S—, —CO—, —CO—O—, —O—CO—, —O—CO—O— or —CH=CH—, provided that heteroatoms are not connected directly, except as permitted in the listed groups;

A and B are each independently selected from the group consisting of: 1,4-cyclohexylene, in which one —$CH_2$— or two not directly linked —$CH_2$— are optionally replaced by —O— or —S—; 1,4-cyclohexenylene; piperidine-1,4-diyl; 1,4-bicyclo[2,2,2]octylene; 1,4-phenylene, which is optionally substituted with one or more halogens; pyridin-5,2-diyl; pyrimidin-5,2-diyl; naphthalene-2,6-diyl; trans-decahydronaphthalene-2,6-diyl; tetrahydronaphthalene-2,6-diyl; indanediyl; indenediyl; phenanthrenediyl; and dibenzofurandiyl, each of which groups independently is optionally substituted with one or more halogens and/or one or more $X_1$-$X_4$ substituents;

$Z_1$ is a single bond or $C_1$-$C_7$ unsubstituted or substituted alkylene, wherein the substitutions are independently one or more of halogen or CN, and wherein one or more of the alkylene groups each independently is optionally replaced by —O—, —S—, —CO—O—, —O—CO—, —O—CO—O—, —CF=CF— or —CH=CH—, provided that heteroatoms are not connected directly to each other except as permitted in the listed groups;

$Z_2$ and $Z_3$ are each independently selected from the group consisting of: a single bond, —$(CH_2)_2$—, —$(CH_2)_4$—, —CH=CHCH$_2$CH$_2$—, —CH$_2$CH$_2$CH=CH—, —CF$_2$O—, —OCF$_2$—, —CF$_2$CF$_2$—, —CF=CF—, —CH$_2$CF$_2$—, —CF$_2$CH$_2$—, —OCF$_2$CF$_2$O—, —C$_2$H$_4$CF$_2$O—, —CH$_2$CF$_2$OCH$_2$—, —CH$_2$OCF$_2$CH$_2$—, —OCF$_2$C$_2$H$_4$—, —C$_3$H$_6$O—, —OC$_3$H$_6$—, —C$_2$H$_4$OCH$_2$—, —CH$_2$OC$_2$H$_4$—, —CH$_2$O—, —OCH$_2$—, —CH=CH—, —C≡C—, and —COO—; provided that when $Z_1$ is —OCH$_2$—, —OC(=O)— or —CH$_2$—CH$_2$—, $Z_2$ or $Z_3$ cannot be —OC(=O)—, —OCH$_2$—, —CH$_2$—CH$_2$—, —OC$_2$H$_6$—, —C$_4$H$_8$—, —C≡C—, or a single bond;

n is 1 or 2;

m and K are each independently 0, 1, or 2, and m+K+n≥2;

each $X_1$, $X_2$, $X_3$, and $X_4$ is independently selected from the group consisting of: hydrogen, —F, —Cl, —CF$_3$, —CHF$_2$, —OCF$_3$, —OCF$_2$H and —CN;

Y is independently selected from the group consisting of: hydrogen, —F, —Cl, —CN, —NCS, —OCHF$_2$, —CHF$_2$, —OCF$_3$, —OCF$_2$CF$_3$, —CF$_3$, C$_{1-20}$ alkyl, C$_{1-20}$ alkoxy, C$_{1-20}$ alkenyl, and C$_{1-20}$ alkenyloxy, wherein the alkyl, alkoxy, alkenyl, and alkenyloxy groups independently are optionally substituted by one or more halogens;

wherein one or more hydrogen atoms in the compound is optionally replaced with deuterium;

provided that when R is hydrogen and Y has less than 2 carbon atoms and X$_3$, and X$_4$ are both hydrogen or when R is hydrogen and Y has two or more carbon atoms and Z$_1$ has more than 3 carbon atoms, there must be a fused ring system present in the compound or one of Z$_2$ and Z$_3$ must be selected from the group consisting of: —CH=CHCH$_2$CH$_2$—, —CH$_2$CH$_2$CH=CH—, —CF$_2$O—, —OCF$_2$—, —CF$_2$CF$_2$—, —CF=CF—, —CH$_2$CF$_2$—, —CF$_2$CH$_2$—, —OCF$_2$CF$_2$O—, —C$_2$H$_4$CF$_2$O—, —CH$_2$CF$_2$OCH$_2$—, —CH$_2$OCF$_2$CH$_2$—, —OCF$_2$C$_2$H$_4$—, —C$_3$H$_6$O—, —OC$_3$H$_6$—, —C$_2$H$_4$OCH$_2$—, —CH$_2$OC$_2$H$_4$, and —CH=CH—;

and provided that when R is not hydrogen and Y does not contain a —CF$_2$— group and X$_3$ and X$_4$ are hydrogen, either:

one of A and B must be selected from the group consisting of: 1,4-cyclohexylene, in which one or two not directly linked —CH$_2$— groups are optionally replaced by —O— or —S—; pyridin-5,2-diyl; pyrimidin-5,2-diyl; indanediyl; indenediyl; phenanthrenediyl, and dibenzofurandiyl; or one of Z$_1$, Z$_2$ and Z$_3$ must be selected from the group consisting of: —(CH$_2$)$_4$—, —CH=CHCH$_2$CH$_2$—, —CH$_2$CH$_2$CH=CH—, —CF$_2$O—, —OCF$_2$—, —CF$_2$CF$_2$—, —CF=CF—, —CH$_2$CF$_2$—, —CF$_2$CH$_2$—, —OCF$_2$CF$_2$O—, —C$_2$H$_4$CF$_2$O—, —CH$_2$CF$_2$OCH$_2$—, —CH$_2$OCF$_2$CH$_2$—, —OCF$_2$C$_2$H$_4$—, —C$_3$H$_6$O—, —OC$_3$H$_6$—, —C$_2$H$_4$OCH$_2$—, —CH$_2$OC$_2$H$_4$—, —CH=CH—, and —C≡C—.

2. The compound of claim 1 having a positive dielectric constant.

3. The compound of claim 1 having a negative dielectric constant.

4. A liquid crystal mixture having positive dielectric constant comprising a compound of claim 1.

5. The mixture of claim 4, wherein the mixture further comprises at least one compound of formula II-XVI

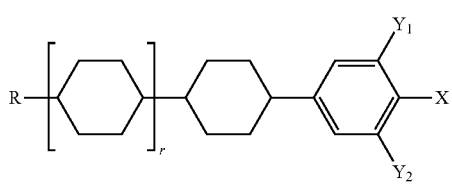

II

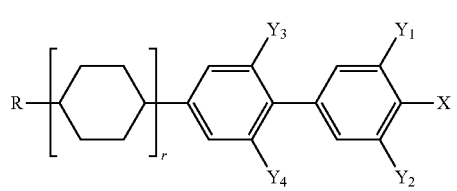

III

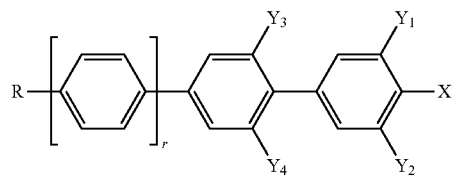

IV

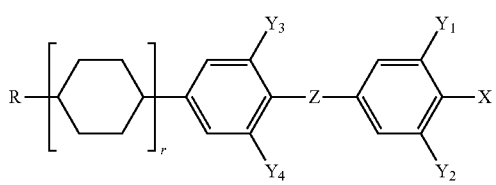

V

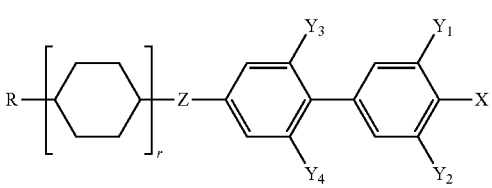

VI

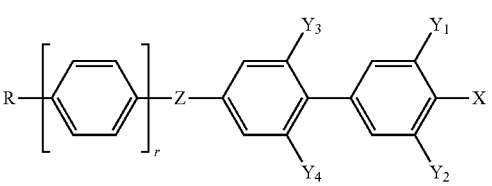

VII

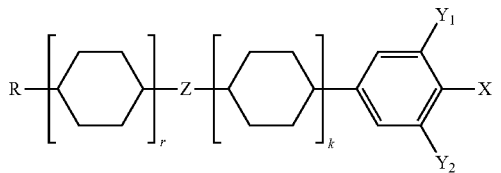

VIII

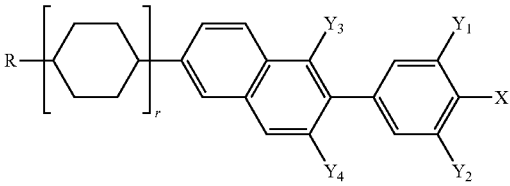

IX

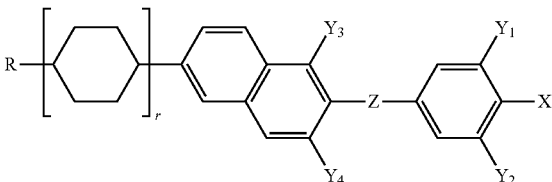

X

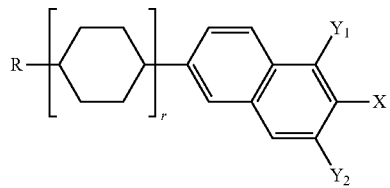

XI

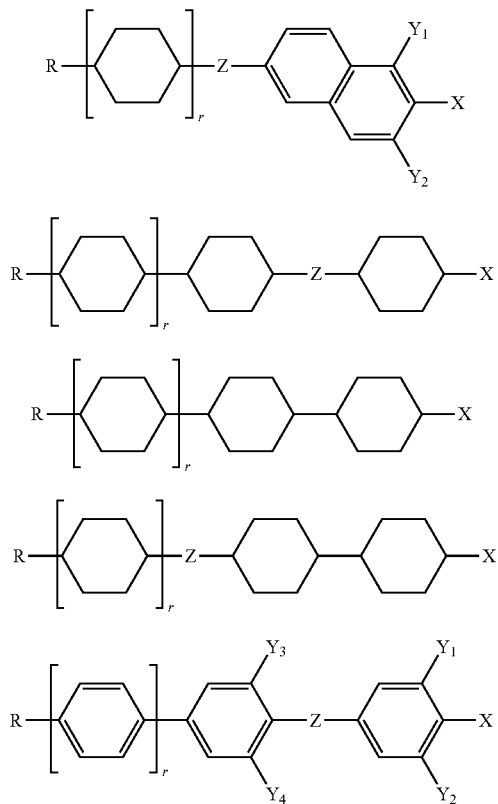

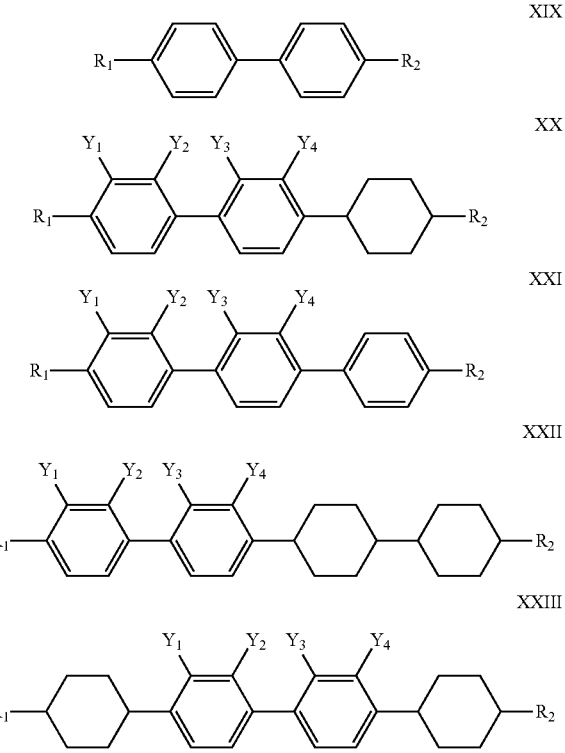

in which the variables for formulas II-XVI have the following definitions:

R is $C_1$-$C_9$ n-alkyl, $C_1$-$C_9$ alkoxy, $C_1$-$C_9$ oxaalkyl, $C_1$-$C_9$ fluoroalkyl or $C_1$-$C_9$ alkenyl;

X is —F, —Cl, halogenated $C_1$-$C_6$ alkyl, halogenated $C_1$-$C_6$ alkenyl, halogenated $C_1$-$C_6$ alkenyloxy or halogenated $C_1$-$C_6$ alkoxy;

Z is —$C_2H_4$—, —$C_4H_8$—, —CH=CH—, —$CH_2$O—, —COO—, —$OCH_2$—, —$OCF_2$—, —$CF_2$O—, —CF=CF—, —$C_2F_4$—, —$CH_2CF_2$— or —$CF_2CH_2$—;

each $Y_1$, $Y_2$, $Y_3$ and $Y_4$ is, independently of one another, hydrogen or —F; and r is 0, 1 or 2; and k is 0 or 1, provided that, if both r and k appear in the same formula, r+k≥2.

6. The mixture of claim 4, wherein the mixture further comprises at least one compound of formula XVII-XXIII

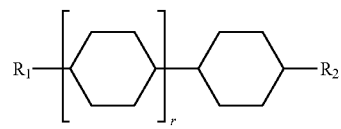

XVII

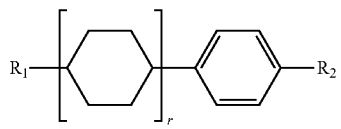

XVIII in which the variables for formulas XVII-XXII have the following definitions:

$R_1$ and $R_2$ are independently $C_1$-$C_9$ n-alkyl, $C_1$-$C_9$ alkoxy, $C_1$-$C_9$ oxaalkyl, or $C_1$-$C_9$ alkenyl;

each $Y_1$, $Y_2$, $Y_3$ and $Y_4$ are, independently of one another, H or F, and r is 0, 1 or 2.

7. The mixture of claim 4, wherein the mixture comprises at least one compound of formula II-XVI

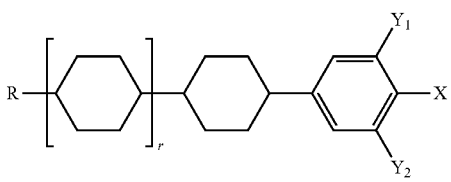

II

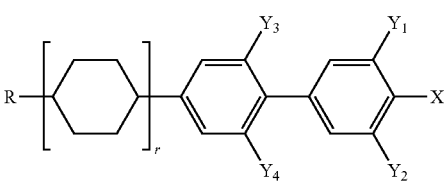

III

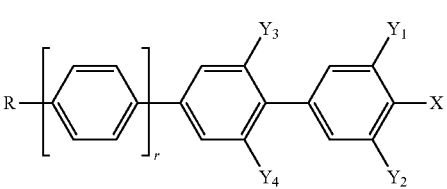

IV

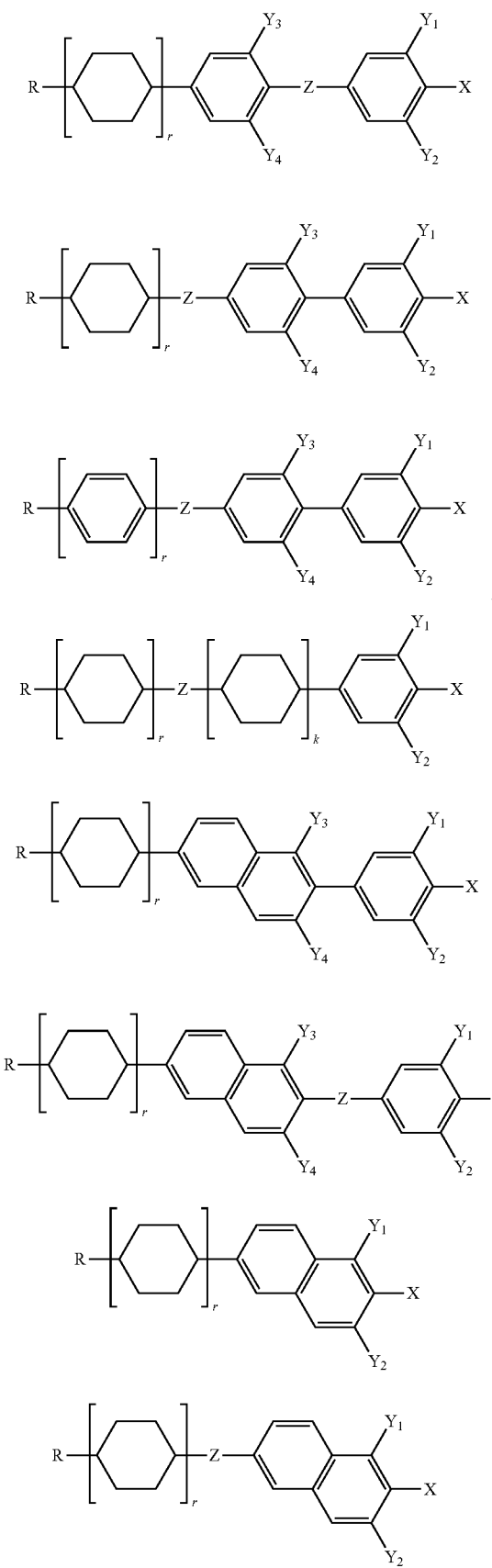
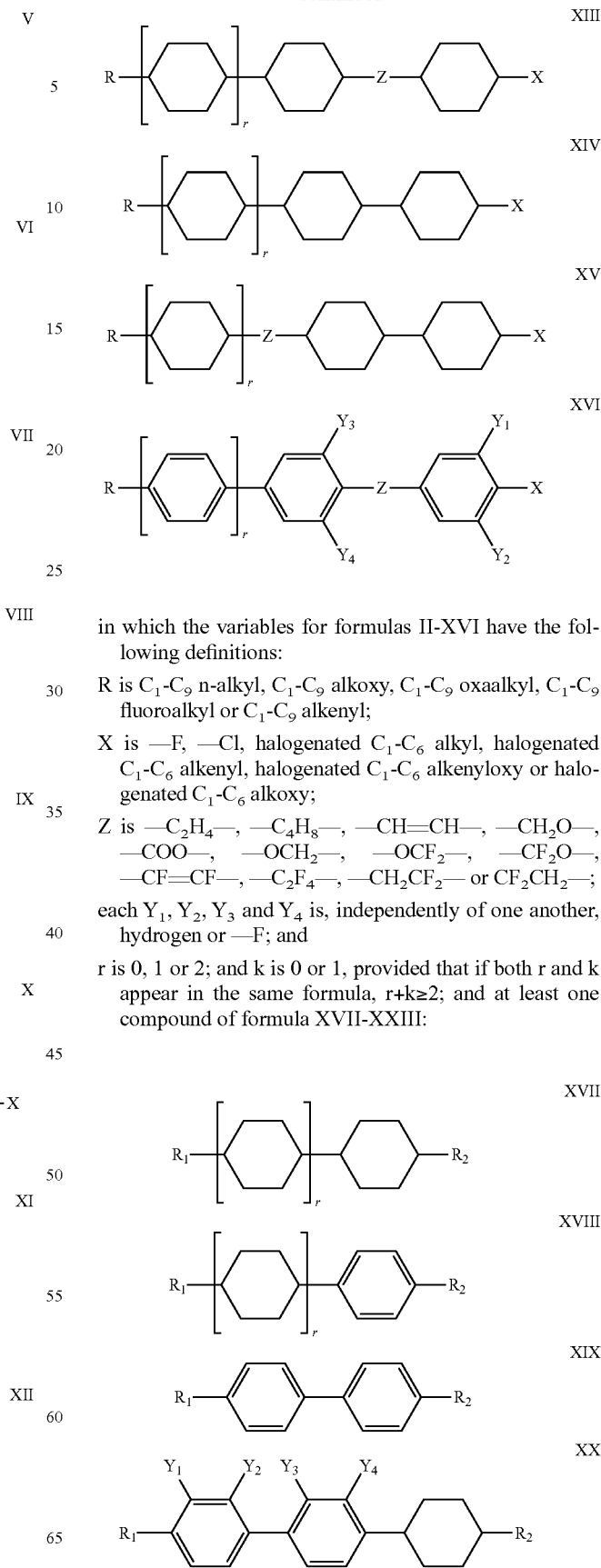

in which the variables for formulas II-XVI have the following definitions:

R is $C_1$-$C_9$ n-alkyl, $C_1$-$C_9$ alkoxy, $C_1$-$C_9$ oxaalkyl, $C_1$-$C_9$ fluoroalkyl or $C_1$-$C_9$ alkenyl;

X is —F, —Cl, halogenated $C_1$-$C_6$ alkyl, halogenated $C_1$-$C_6$ alkenyl, halogenated $C_1$-$C_6$ alkenyloxy or halogenated $C_1$-$C_6$ alkoxy;

Z is —$C_2H_4$—, —$C_4H_8$—, —CH=CH—, —$CH_2O$—, —COO—, —$OCH_2$—, —$OCF_2$—, —$CF_2O$—, —CF=CF—, —$C_2F_4$—, —$CH_2CF_2$— or $CF_2CH_2$—;

each $Y_1$, $Y_2$, $Y_3$ and $Y_4$ is, independently of one another, hydrogen or —F; and r is 0, 1 or 2; and k is 0 or 1, provided that if both r and k appear in the same formula, r+k≥2; and at least one compound of formula XVII-XXIII:

-continued

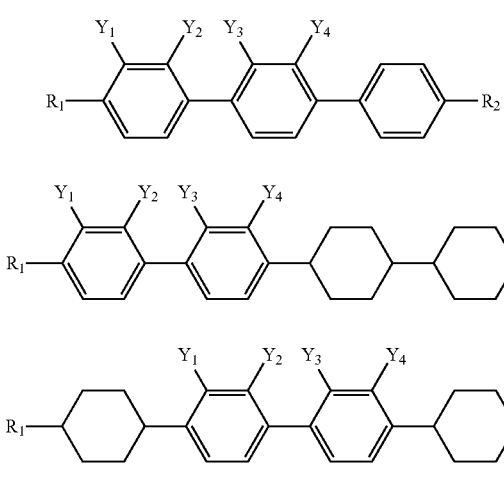

XXI

XXII

XXIII in which the variables for formulas XVII-XXIII have the following definitions:

$R_1$ and $R_2$ are each independently $C_1$-$C_9$ n-alkyl, $C_1$-$C_9$ alkoxy, $C_1$-$C_9$ oxaalkyl, or $C_1$-$C_9$ alkenyl;

each $Y_1$, $Y_2$, $Y_3$ and $Y_4$ is, independently of one another, hydrogen or —F, and r is 0, 1 or 2.

8. A liquid crystal mixture having negative dielectric constant comprising a compound of claim 1.

9. The mixture of claim 8, wherein the mixture further comprises at least one compound of formula XXIV-XLIV

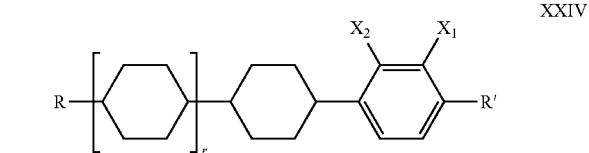

XXIV

XXV

XXVI

XXVII

XXVIII

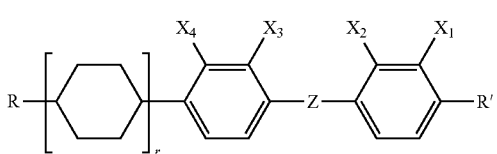

XXIX

XXX

XXXI

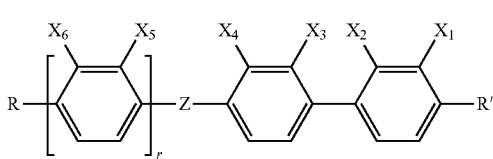

XXXII

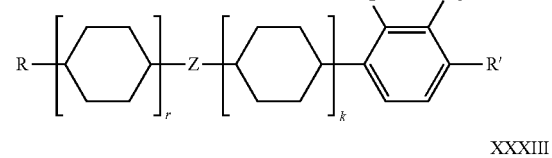

XXXIII

XXXIV

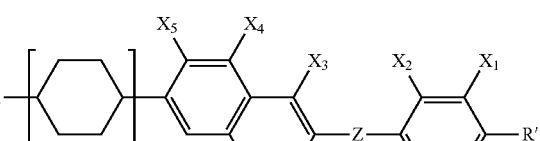

XXXV

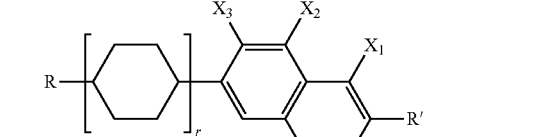

XXXVI

XXXVII

-continued

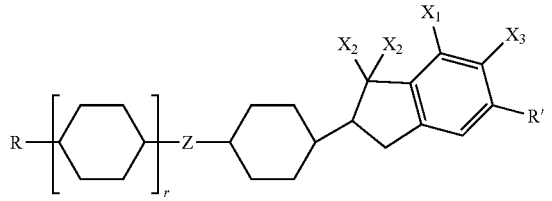
XXXVIII

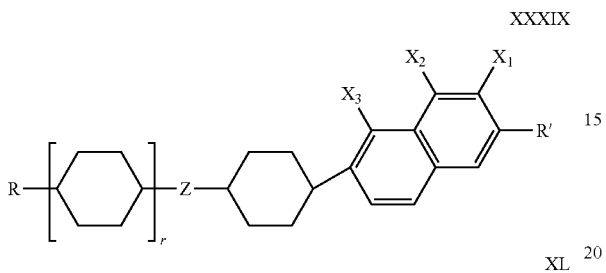
XXXIX

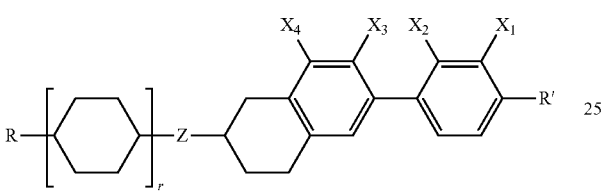
XL

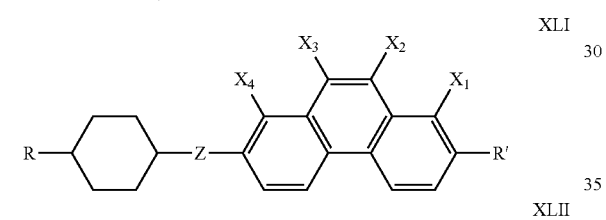
XLI

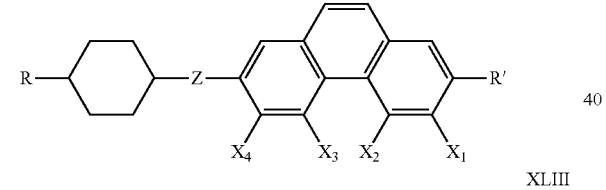
XLII

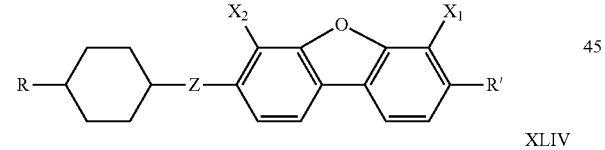
XLIII

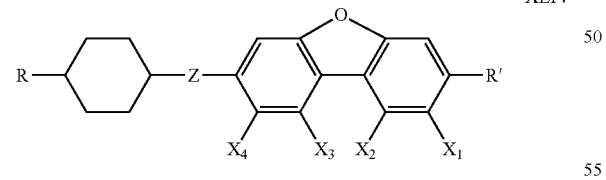
XLIV in which the variables for formulas XXIV-XLIV have the following definitions:

R is $C_1$-$C_8$ n-alkyl, $C_1$-$C_8$ alkoxy, $C_1$-$C_8$ alkenyl or $C_1$-$C_8$ alkenyloxy;

R' is $C_1$-$C_8$ alkyl, $C_1$-$C_8$ alkoxy, $C_1$-$C_8$ alkenyl or $C_1$-$C_8$ alkenyloxy;

each $X_1$, $X_2$, $X_3$, $X_4$, $X_5$ and $X_6$ is independently selected from the group consisting of: hydrogen, —F, —Cl, —CHF$_2$, —CF$_3$, —OCF$_3$ and —OCHF$_2$; with the proviso that at least two of $X_1$ to $X_6$ are —F, —Cl, —CHF$_2$, or —CF$_3$;

Z is independently selected from the group consisting of: single bond, —C$_2$H$_4$—, —C$_4$H$_8$—, —CH=CHCH$_2$CH$_2$—, —CH$_2$CH$_2$CH=CH—, —CF$_2$O—, —OCF$_2$—, —CF=CF—, —C$_2$F$_4$—, —C$_2$H$_4$CF$_2$O—, —OCF$_2$C$_2$H$_4$— and —CO$_2$—;

r is 0, 1 or 2; k is 0 or 1, and r+k≥2.

10. The mixture of claim 8, wherein the mixture further comprises at least one compound of formula XLV-XLVIII

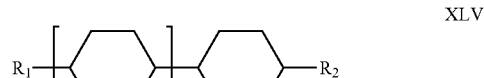
XLV

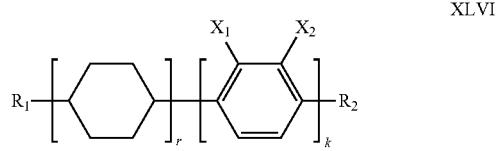
XLVI

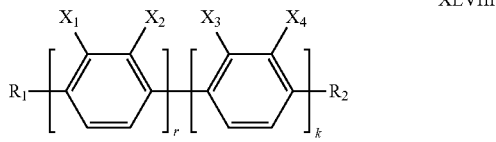
XLVII

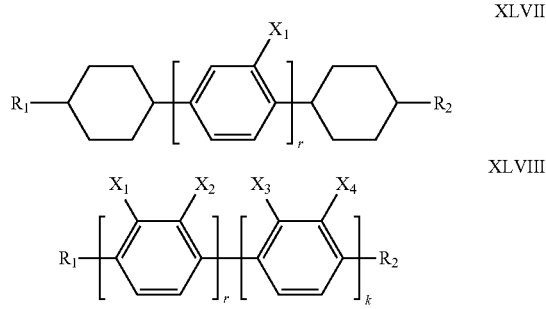
XLVIII in which the variables for formulas XLV-XLVIII are defined as follows:

$R_1$ and $R_2$ are each independently $C_1$-$C_8$ n-alkyl, $C_1$-$C_8$ alkoxy, $C_1$-$C_8$ oxaalkyl, $C_1$-$C_8$ alkenyl, or $C_1$-$C_8$ alkenyoxy;

each $X_1$, $X_2$, $X_3$, and $X_4$ is hydrogen or —F, provided that only one of $X_1$, $X_2$, $X_3$, and $X_4$ is —F in the same compound;

r is 1 or 2; and k is 1 or 2.

11. The mixture of claim 8, wherein the mixture further comprises at least one compound of formula XXIV-XLIV

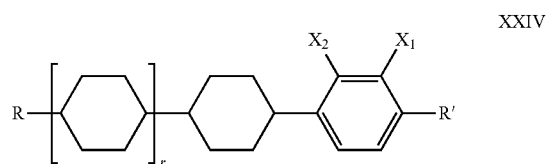
XXIV

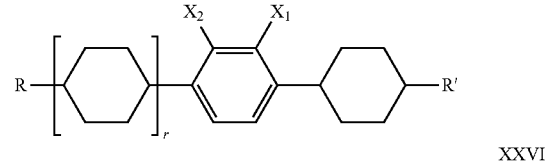
XXV

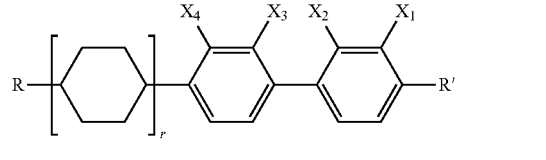
XXVI

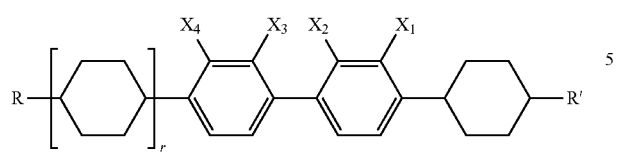 XXVII
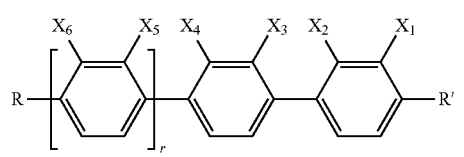 XXVIII
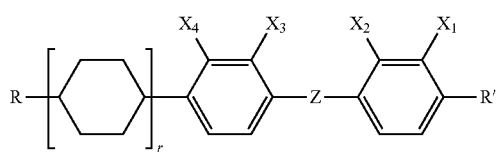 XXIX
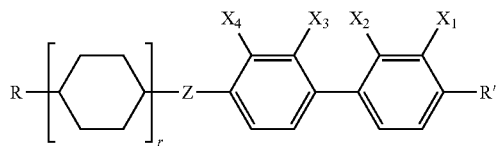 XXX
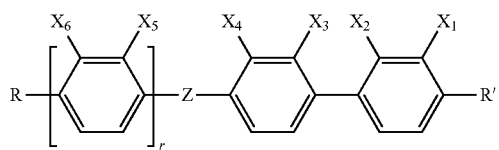 XXXI
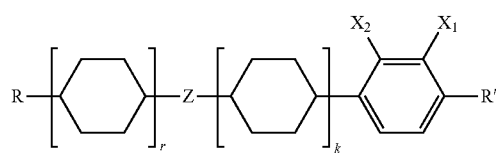 XXXII
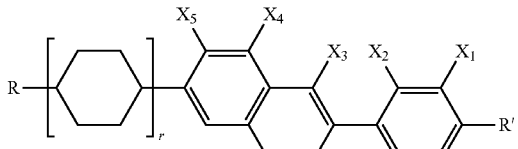 XXXIII
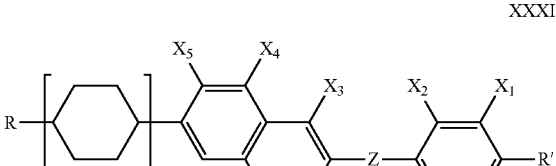 XXXIV
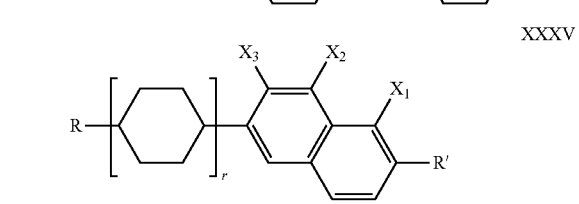 XXXV
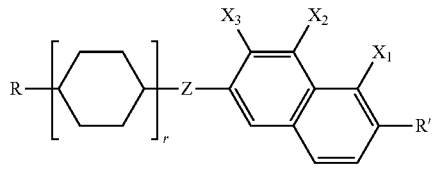 XXXVI
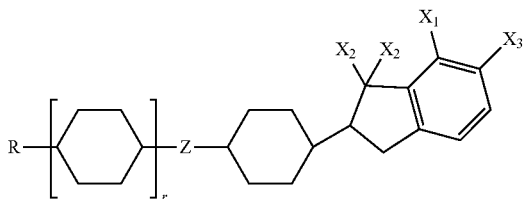 XXXVII
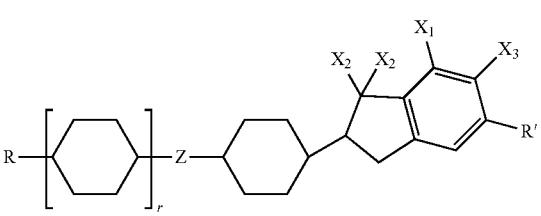 XXXVIII
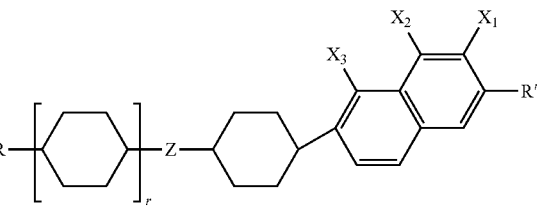 XXXIX
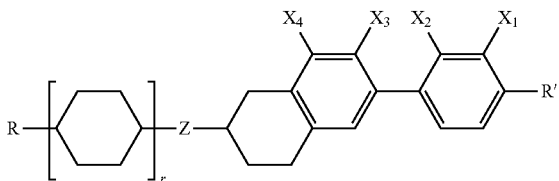 XL
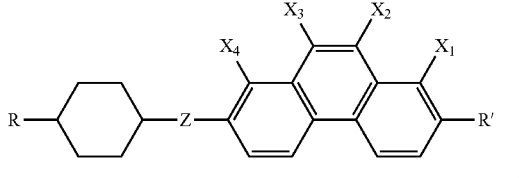 XLI
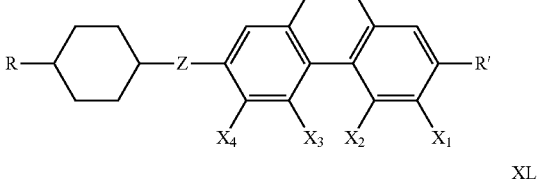 XLII
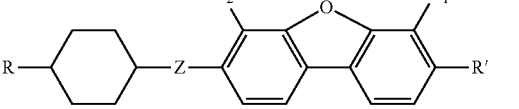 XLIII

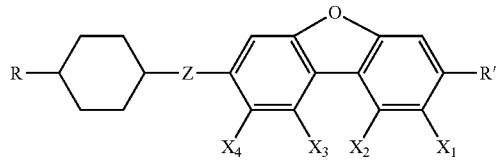

XLIV in which the variables for formulas XXIV-XLIV are defined as follows:

R is $C_1$-$C_8$ n-alkyl, $C_1$-$C_8$ alkoxy, $C_1$-$C_8$ alkenyl or $C_1$-$C_8$ alkenyloxy;

R' is $C_1$-$C_8$ alkyl, $C_1$-$C_8$ alkoxy, $C_1$-$C_8$ alkenyl or $C_1$-$C_8$ alkenyloxy;

each $X_1$, $X_2$, $X_3$, $X_4$, $X_5$ and $X_6$ is independently selected from the group consisting of: hydrogen, —F, —Cl, —CHF$_2$, —CF$_3$, —OCF$_3$ and —OCHF$_2$ provided that at least two of $X_1$-$X_6$ are —F, —Cl, —CHF$_2$, —CF$_3$, —OCF$_3$ and —OCHF$_2$;

Z is independently selected from the group consisting of: single bond, —C$_2$H$_4$—, —C$_4$H$_8$—, —CH=CHCH$_2$CH$_2$—, —CH$_2$CH$_2$CH=CH—, —CF$_2$O—, —OCF$_2$—, —CF=CF—, —C$_2$F$_4$—, —C$_2$H$_4$CF$_2$O—, —OCF$_2$C$_2$H$_4$ and —CO$_2$—;

r is 0, 1 or 2; k is 0 or 1, and r+k≥2; and at least one compound of formula XLV-XLVIII

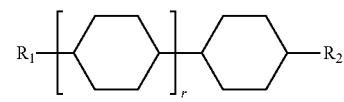

XLV

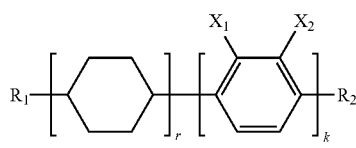

XLVI

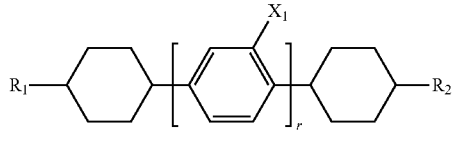

XLVII

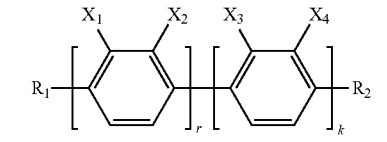

XLVIII in which the variables for formulas XLV-XLVIII are as follows:

$R_1$ and $R_2$ are each independently $C_1$-$C_8$ n-alkyl, $C_1$-$C_8$ alkoxy, $C_1$-$C_8$ oxaalkyl, $C_1$-$C_8$ alkenyl, or $C_1$-$C_8$ alkenyoxy;

each $X_1$, $X_2$, $X_3$, and $X_4$ is hydrogen or —F, provided that only one of $X_1$, $X_2$, $X_3$, and $X_4$ is —F in the same compound;

r is 1 or 2; and k is 1 or 2.

12. A device comprising a compound of claim 1.

13. A compound of formula:

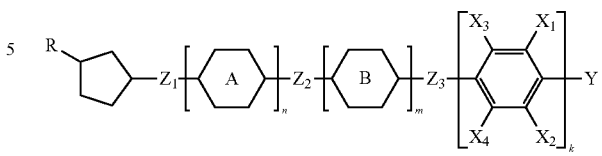

wherein:
R is hydrogen or a $C_{1-12}$ unsubstituted alkyl group;
$Z_1$ and $Z_2$ are single bonds and $Z_3$ is —CF$_2$O—;
each $X_1$, $X_2$, $X_3$, and $X_4$ is independently selected from hydrogen, —F, —CF$_3$, and —OCF$_3$;
each A and B ring is independently selected from: 1,4-cyclohexylene, in which one —CH$_2$— or two not directly linked —CH$_2$— are optionally replaced by —O—; 1,4-phenylene; or naphthalene-2,6-diyl; each of which rings are optionally substituted with one or more halogens;
Y is selected from the group consisting of:
hydrogen, —F, —OCHF$_2$, —CHF$_2$, —OCF$_3$, —OCF$_2$CF$_3$, or —CF$_3$, or
$C_{1-20}$ alkyl, $C_{1-20}$ alkoxy, $C_{1-20}$ alkenyl, or $C_{1-20}$ alkenyloxy, wherein each of these groups are optionally substituted by one or more halogens;
n is 1 or 2;
K is 1 or 2;
m is 0, 1 or 2; and
n+K+m≥2.

14. The compound of claim 13 wherein:
each $X_1$, and $X_2$ is independently selected from hydrogen or —F; and
each $X_3$ and $X_4$ is a hydrogen; and
Y is selected from hydrogen, —F, —OCHF$_2$, —OCF$_3$, or —CF$_3$.

15. The compound of claim 14 wherein each A and B ring is selected from 1,4-cyclohexylene or 1,4-phenylene rings which are optionally substituted with one or more halogens.

16. The compound of claim 14 where K is 1.

17. The compound of claim 14 where K is 2.

18. The compound of claim 14 where R is hydrogen.

19. The compound of claim 14 where R is a $C_1$-$C_{12}$ alkyl.

20. The compound of claim 13 wherein:
each $X_1$ and $X_3$ is independently selected from —F, —CF$_3$, or —OCF$_3$;
each $X_2$ and $X_4$ is independently selected from hydrogen, —F, —CF$_3$, or —OCF$_3$; and
Y is selected from the group consisting of —F, $C_{1-20}$ alkyl, $C_{1-20}$ alkoxy, $C_{1-20}$ alkenyl, and $C_{1-20}$ alkenyloxy, wherein each group is optionally substituted by one or more halogens.

21. The compound of claim 20 wherein each A and B ring is selected from 1,4-cyclohexylene or 1,4-phenylene rings which are optionally substituted with one or more halogens.

22. The compound of claim 20 where K is 1.

23. The compound of claim 20 where K is 2.

24. The compound of claim 20 where R is hydrogen.

25. The compound of claim 20 where R is a $C_1$-$C_{12}$ alkyl.

26. The compound of claim 1 wherein one of the A or B rings is selected from the group consisting of: 1,4-bicyclo[2,2,2]octylene; naphthalene-2,6-diyl; trans-decahydronaphthalene-2,6-diyl; tetrahydronaphthalene-2,6-diyl; indanediyl; indenediyl; phenanthrenediyl; and dibenzofurandiyl each of which is optionally substituted with one or more halogens.

27. The compound of claim 26 wherein K is 0.

28. The compound of claim 1 having a formula selected from:

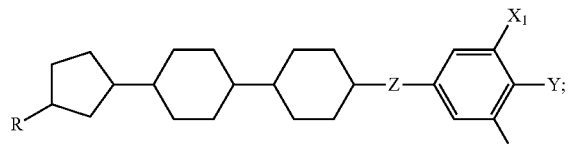

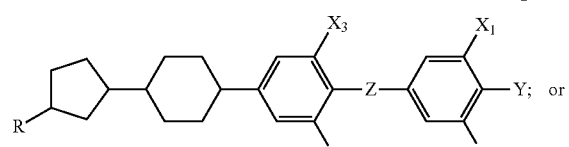

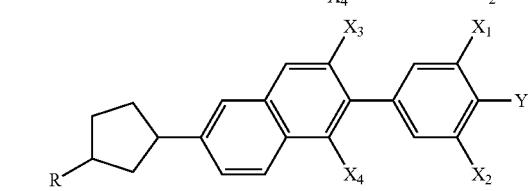

where for these formulas the variable definitions are as follows:

Y is independently selected from the group consisting of: —F, —Cl, —CF$_3$, —OCF$_3$, —OCHF$_2$—OCF$_2$CF$_3$, —OCF=CF$_2$, —OCHFCF$_3$, and —OCF$_2$CF=CF$_2$;

X$_1$, X$_2$, X$_3$, X$_4$ are each, independently of one another, —H or —F;

Z is independently selected from the group consisting of: single bond, —C$_2$H$_4$—, —CF$_2$O—, —CF=CF—, —C$_2$F$_4$—; —CO$_2$—; —C$_4$H$_8$—, —C$_2$H$_4$CF$_2$O—, —OCF$_2$CF$_2$O—, —CH=CHCH$_2$CH$_2$—, —CH$_2$CH$_2$CH=CH—; and R is hydrogen or a C$_1$-C$_{12}$ alkyl; or

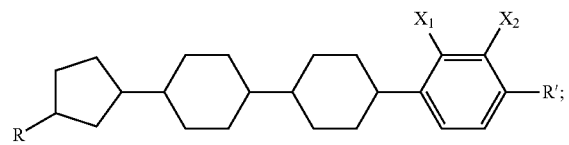

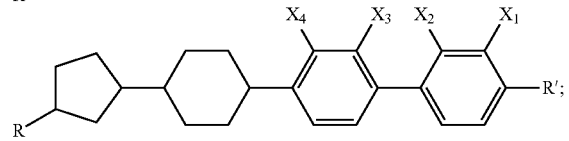

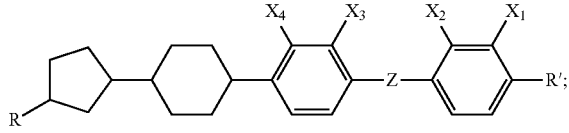

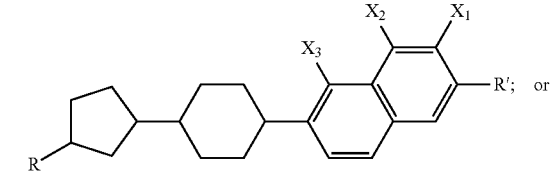

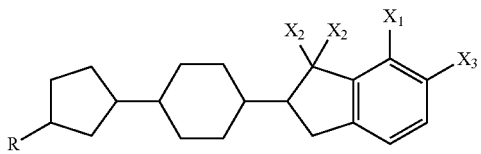

where for these formulas the variable definitions are as follows:

R is H or C$_1$-C$_7$ n-alkyl;

R' is C$_1$-C$_7$ n-alkyl or C$_1$-C$_7$ Alkyloxy;

X$_1$ and X$_2$ are each independently selected from the group consisting of —F, —Cl, —CF$_3$, —CHF$_2$—OCF$_3$ and —OCF$_2$H;

X$_3$ and X$_4$ are each independently H or F; and

Z is independently single bond, —C$_2$H$_4$—, —C$_4$H$_8$—, —CF$_2$O—, —CF=CF—, —C$_2$F$_4$—, C$_2$H$_4$CF$_2$O or —CO$_2$—.

29. The compound of claim 1 having a formula selected from formula I-1 through I-17:

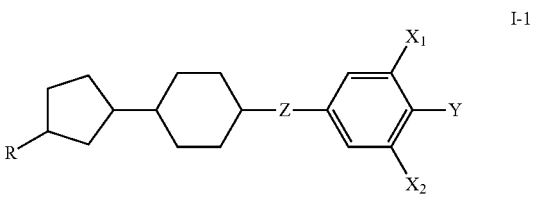

I-1

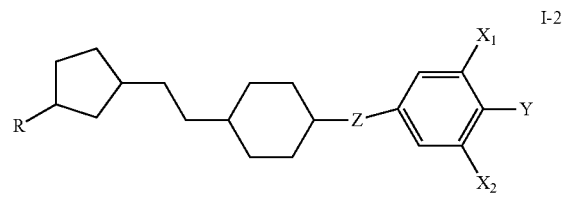

I-2

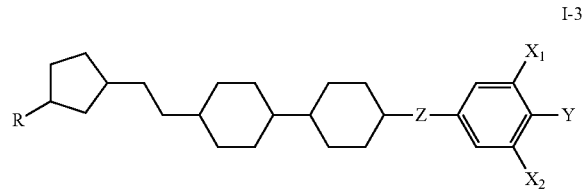

I-3

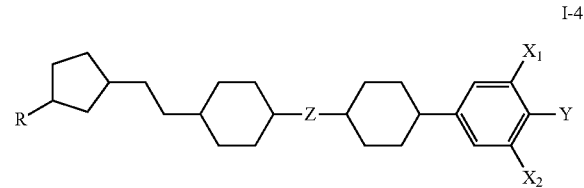

I-4

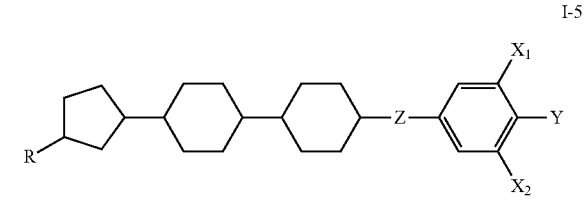

I-5

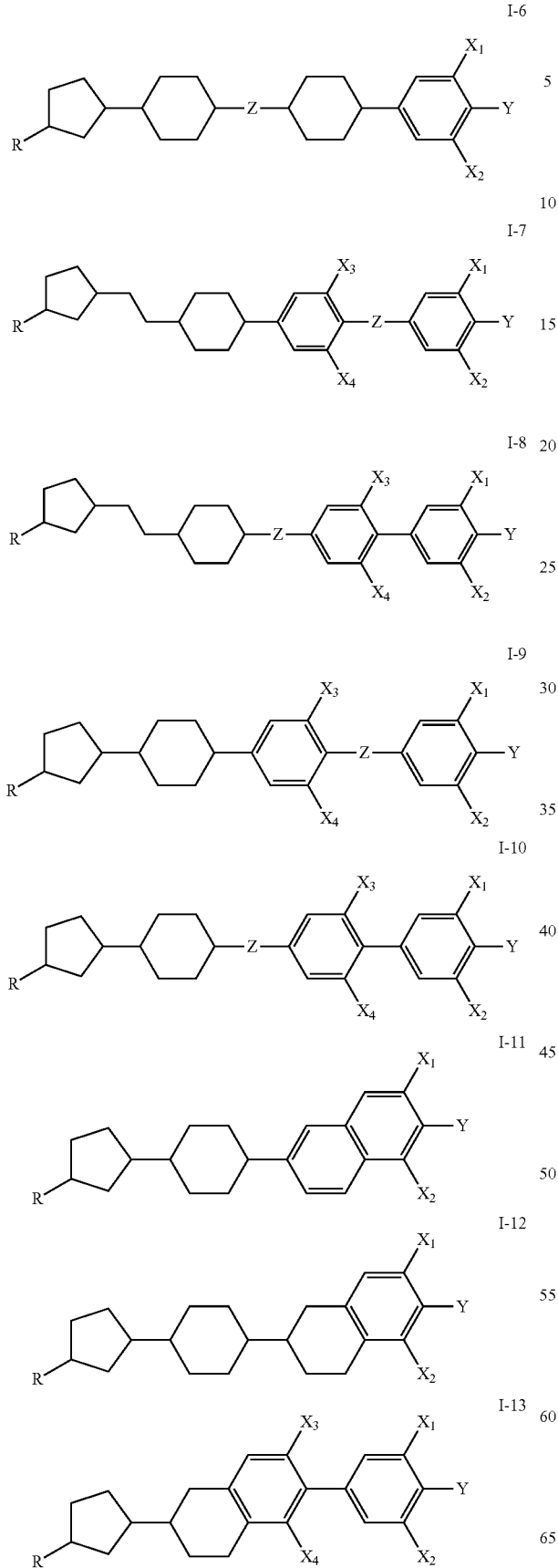
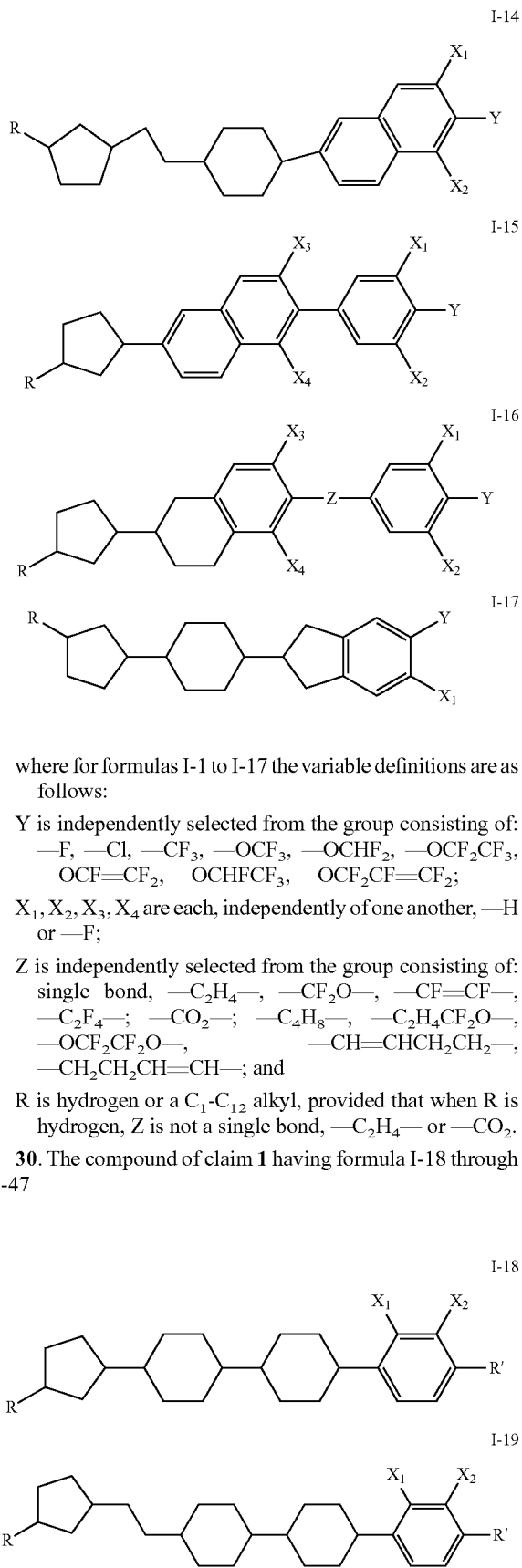

where for formulas I-1 to I-17 the variable definitions are as follows:

Y is independently selected from the group consisting of: —F, —Cl, —CF$_3$, —OCF$_3$, —OCHF$_2$, —OCF$_2$CF$_3$, —OCF=CF$_2$, —OCHFCF$_3$, —OCF$_2$CF=CF$_2$;

X$_1$, X$_2$, X$_3$, X$_4$ are each, independently of one another, —H or —F;

Z is independently selected from the group consisting of: single bond, —C$_2$H$_4$—, —CF$_2$O—, —CF=CF—, —C$_2$F$_4$—; —CO$_2$—; —C$_4$H$_8$—, —C$_2$H$_4$CF$_2$O—, —OCF$_2$CF$_2$O—, —CH=CHCH$_2$CH$_2$—, —CH$_2$CH$_2$CH=CH—; and R is hydrogen or a C$_1$-C$_{12}$ alkyl, provided that when R is hydrogen, Z is not a single bond, —C$_2$H$_4$— or —CO$_2$.

30. The compound of claim 1 having formula I-18 through I-47

I-20 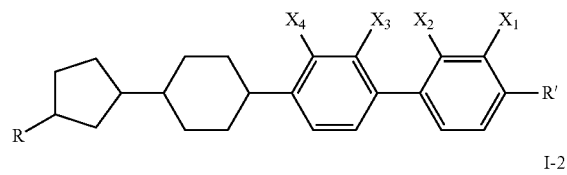
I-21 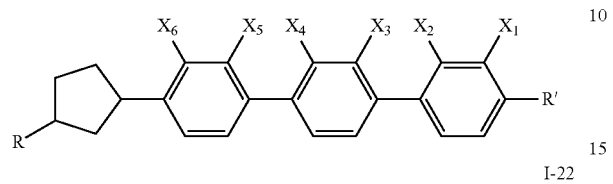
I-22 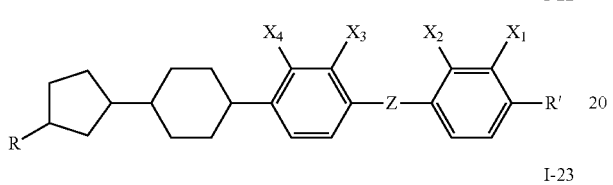
I-23 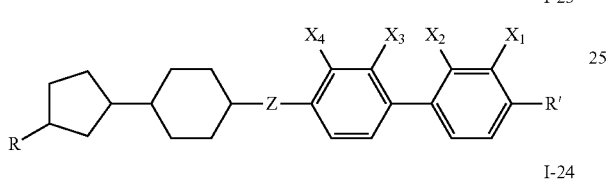
I-24 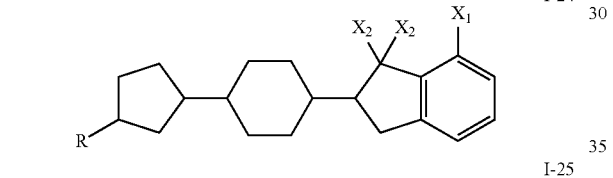
I-25 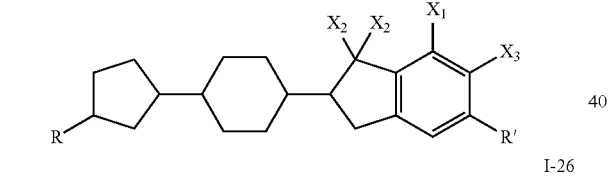
I-26 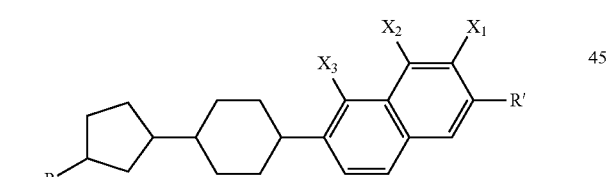
I-27 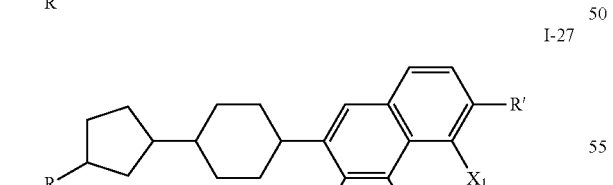
I-28 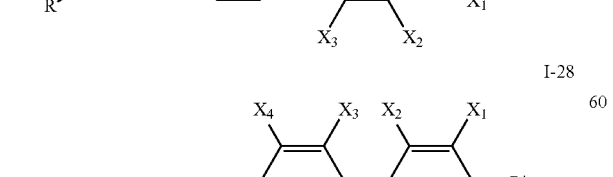
I-29 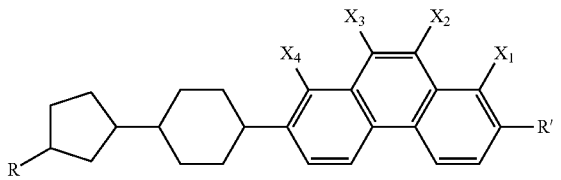
I-30 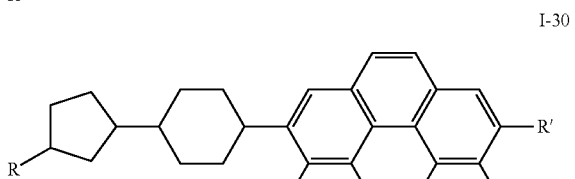
I-31 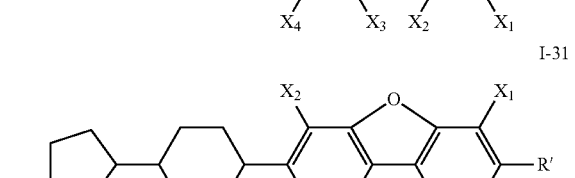
I-32 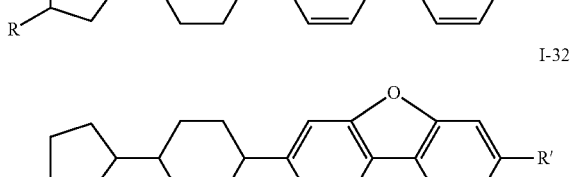
I-33 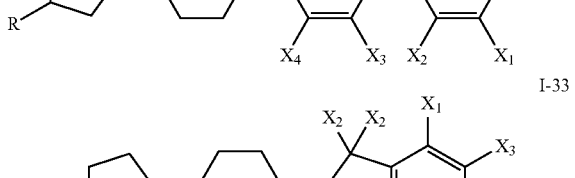
I-34 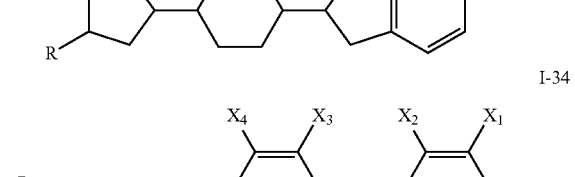
I-35 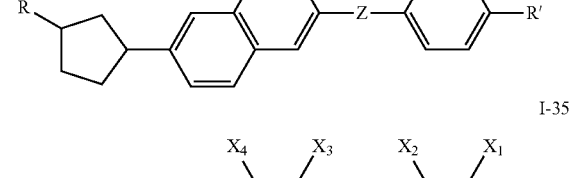
I-36 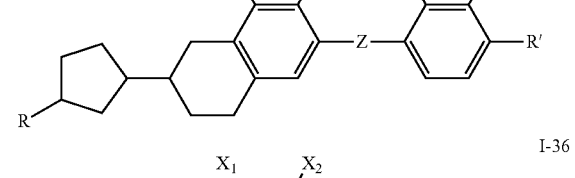
I-37

I-38
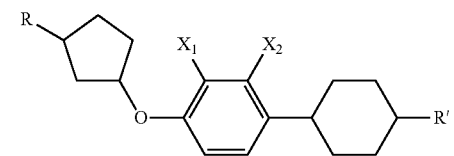

I-39
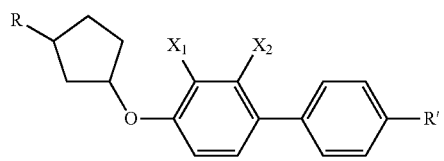

I-40
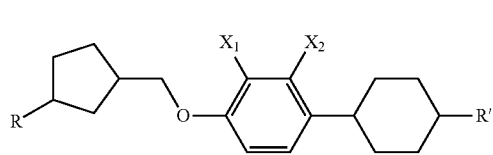

I-41
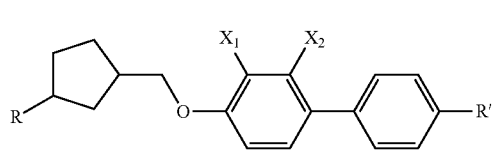

I-42
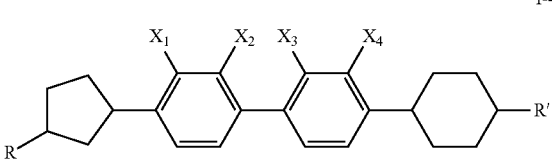

I-43

I-44
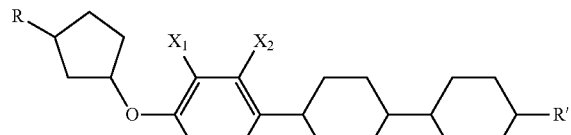

I-45
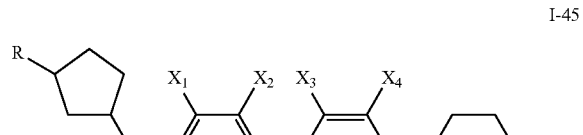

I-46
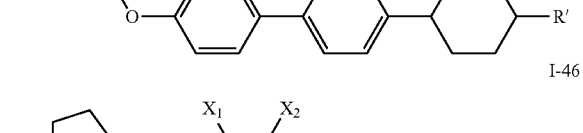

I-47
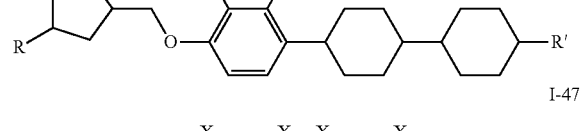

where for formulas I-18 to I-47 variable definitions are as follows:

R is hydrogen; $C_1$-$C_7$ n-alkyl or $C_1$-$C_7$ alkenyl;

R' is $C_1$-$C_7$ n-alkyl, $C_1$-$C_7$ n-alkenyl, $C_1$-$C_7$ alkyloxy, or $C_1$-$C_7$ n-alkenyloxy;

$X_1$ and $X_2$ are each independently selected from the group consisting of hydrogen, —F, —Cl, —$CF_3$, —$CHF_2$, —$OCF_3$ and —$OCF_2H$;

$X_3$, $X_4$, $X_5$ and $X_6$ are each independently hydrogen or —F; and

Z is independently a single bond, —$C_2H_4$—, —$C_4H_8$—, —$CF_2O$—, —CF=CF—, —CH=CH—, —$C_2F_4$—, —$C_2H_4CF_2O$— or —$CO_2$—.

* * * * *